US008114976B2

(12) United States Patent
Buck et al.

(10) Patent No.: US 8,114,976 B2
(45) Date of Patent: Feb. 14, 2012

(54) CRYPTOSPORIDIUM HOMINIS GENES AND GENE PRODUCTS FOR CHEMOTHERAPEUTIC, IMMUNOPROPHYLACTIC AND DIAGNOSTIC APPLICATIONS

(75) Inventors: Gregory Buck, Richmond, VA (US); Luis Shozo Ozaki, Richmond, VA (US); Yingping Wang, Richmond, VA (US); Ping Xu, Richmond, VA (US); Myma Garcia Serrano, Richmond, VA (US); Patrico A. Manque, Richmond, VA (US); Joao Marcelo Pereira Alves, Richmond, VA (US); Daniela Puiu, Montgomery Village, MD (US)

(73) Assignee: Virginia Commonwealth University, Richmond, VA (US)

( * ) Notice: Subject to any disclaimer, the term of this patent is extended or adjusted under 35 U.S.C. 154(b) by 709 days.

(21) Appl. No.: 11/575,245

(22) PCT Filed: Sep. 7, 2005

(86) PCT No.: PCT/US2005/031657
§ 371 (c)(1),
(2), (4) Date: Jun. 23, 2009

(87) PCT Pub. No.: WO2006/044045
PCT Pub. Date: Apr. 27, 2006

(65) Prior Publication Data
US 2009/0304732 A1 Dec. 10, 2009

Related U.S. Application Data

(60) Provisional application No. 60/607,356, filed on Sep. 7, 2004.

(51) Int. Cl.
*C07H 21/04* (2006.01)
*C12P 21/06* (2006.01)
(52) U.S. Cl. .................... 536/23.7; 435/69.1; 435/252.3
(58) Field of Classification Search .................... None
See application file for complete search history.

(56) References Cited

U.S. PATENT DOCUMENTS
6,514,697 B1    2/2003  Petersen et al.

OTHER PUBLICATIONS

Crystal RG. Science 270:404-410.1995.*
Orkin SH and Motulsky AG. Report and Recommendations of the Panel to Assess the NIH investment in research on gene therapy, 1995.*
Verma IM and Somia N. Nature 389: 239-242. 1997.*
Anderson WF. Nature 392 (SUPP):25-30, 1998.*
Kmiec EB. American Scientist 87:240-247, 1999.*
Romano et al. Stem Cells 2000; 18:19-39.*
Genembl database of nucleic acid sequences derived from GenBank and EMBL. Accession No. AAEL010000029/AAEL 010000000, Jun. 2004. Abrahamsen et al. Complete Genome Sequence of the Apicomplexan, Cryptosporidium parvum Science Apr. 16, 2004, vol. 304, issue 5669; pp. 441-445.
Ping Xu, et al. The Genome of Cryptosporidum homonis; Nature, Oct. 2004, vol. 431, No. 7012, pp. 1107-1112.

* cited by examiner

*Primary Examiner* — Padma Baskar
(74) *Attorney, Agent, or Firm* — Whitham Curtis Christofferson & Cook, PC

(57) ABSTRACT

*Cryptosporidium hominis* genes and gene products are provided. The genes and gene products are useful for chemotherapeutic, immunotherapeutic, immunoprophylactic and diagnostic applications.

2 Claims, 2 Drawing Sheets

Figure 1:
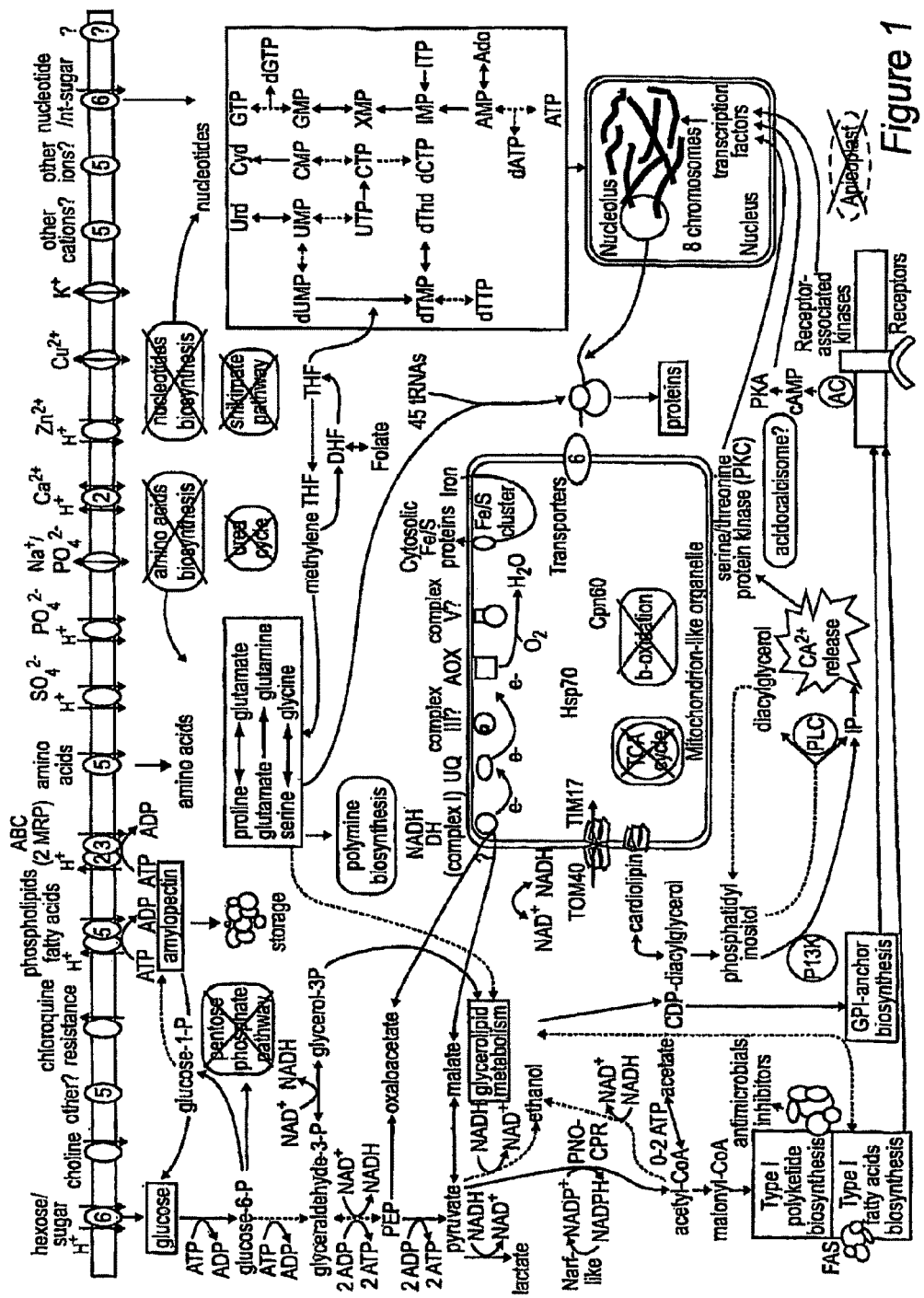

CRYPTOSPORIDIUM HOMINIS GENES AND GENE PRODUCTS FOR CHEMOTHERAPEUTIC, IMMUNOPROPHYLACTIC AND DIAGNOSTIC APPLICATIONS

BACKGROUND OF THE INVENTION

This application is a national stage entry of PCT/US05/31657, International Filing Date: Sep. 7, 2005 and claims priority to Provisional Application 60/607,356, filed Sep. 7, 2004.

STATEMENT OF GOVERNMENT INTEREST

This invention was made with government support under Contract Number 5u1a146416 awarded by the National Institutes of Health, NIAID. The Government has certain rights in the invention.

FIELD OF THE INVENTION

The invention generally relates to *Cryptosporidium hominis* genes and gene products In particular, the invention provides *Cryptosporidium hominis* genes and gene products for use in chemotherapeutic, immunotherapeutic, immunoprophylactic and diagnostic applications.

BACKGROUND OF THE INVENTION

*Cryptosporidium* species are the causative agent of cryptosporidiosis, a disease that is characterized by acute gastro-enteritis and diarrhea. The disease is rampant in many developing countries (e.g. in Latin America, Africa, and Asia). However, incidents of cryptosporidiosis occur worldwide and developing countries are not immune to such incidents. For example, an outbreak in Milwaukee, Wis. in the mid 1990's caused over 400,000 human infections. Thus, no site on earth is free from the threat of serious outbreaks of cryptosporidiosis. Further, the National Institutes of Health and the Center for Disease Control classify *Cryptosporidium* as an important "Category B" agent of potential biological terrorism.

*Cryptosporidium* species are members of the Apicomplexa. These protozoan pathogens invade host cells using a specialized apical complex, and are usually transmitted by an invertebrate vector or intermediate host. Unlike most Apicomplexans, *Cryptosporidium* completes its life cycle in a single host and is transmitted by ingestion of oocysts. Two species, *C. hominis*, and *C. parvum*, which differ in host range, genotype and pathogenicity, are most relevant to humans. *C. hominis* is restricted to humans whereas *C. parvum* also infects other mammal species.

Currently, there are no effective treatments for cryptosporidiosis, and control focuses on eliminating oocysts from water supplies. However, the resistance of the organism to common inexpensive water treatments seriously hampers this method of control. Despite decades of sophisticated molecular analysis of this and related organisms (e.g., Plasmodia (malaria parasites), *Babesia, Eimeria, Toxoplasma*, etc.), no significant advances have been found in treatment or prevention. Thus, traditional approaches of the prior art have thus far failed to identify the proverbial 'Achilles heel' of *Cryptosporidium*, and to provide viable therapies for the prevention or treatment of cryptosporidiosis.

SUMMARY OF THE INVENTION

The present invention is based on the determination of the sequence of the eight chromosome ~9.2 Mb genome of *C. hominis*, and the analysis of that sequence. Using genomics and bioinformatic approaches, a wide array of new targets for therapeutic and diagnostic applications has been identified. Moreover, an accurate view of the overall metabolism of the organism has been obtained, permitting a realistic approach to identification of critical points of attack for therapeutics.

The complement of *C. hominis* protein-coding genes shows a striking concordance with the requirements imposed by the environmental niches the parasite inhabits. Energy metabolism is largely from glycolysis. Options for both aerobic and anaerobic metabolism are available, the former requiring an alternative electron transport system in a simplified mitochondrion. Biosynthesis capabilities are limited, explaining an extensive array of transporters. Evidence of an apicoplast is absent, but genes associated with apical complex organelles are present. *C. hominis* and *C. parvum* exhibit very similar gene complements and phenotypic differences between these parasites must be due to subtle sequence divergence.

The invention thus provides newly identified genes and gene products of *C. hominis* that are of use in chemo and immunotherapy, immunoprophylaxis, and diagnostic applications.

It is an object of this invention to provide amino acid sequences as represented in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, and SEQ ID NO: 24. It is a further object of this invention to provide nucleotide sequences as represented in SEQ ID NO: 1, SEQ ID NO: 3, SEQ ID NO: 5, SEQ ID NO: 7, SEQ ID NO: 9, and SEQ ID NO: 11, SEQ ID NO: 13, SEQ ID NO: 15, SEQ ID NO: 17, SEQ ID NO: 19, SEQ ID NO: 21, SEQ ID NO: 23 and SEQ ID NOS: 25-4000.

The invention further provides a method of detecting and diagnosing *C. hominis* infection in a patient in need thereof. The method comprises the step of obtaining a biological sample from said patient, and amplifying nucleotide sequences from said sample, and determining infection based on whether there are one or more amplicons are produced.

The invention further provides a method for immunizing a patient against *C. hominis* infection. The method comprises the step of administering to the patient a non-virulent *C. hominis* peptide or nucleotide in an amount sufficient to permit the patient to mount an antibody response to the non-virulent *C. hominis* peptide or nucleotide. By non-virulent, we mean that the peptide or nucleotide does not cause pathology (e.g. symptoms of *C. hominis* infection).

The invention further provides a method for detecting *Cryptosporidium* such as *C. hominis* in a sample, for example, of detecting contamination of a water supply by *Cryptosporidium*. The method comprises the steps of 1) obtaining a sample; 2) amplifying nucleotide sequences from the sample; and 3) detecting amplicons produced in the step of amplifying. The production of amplicons in the amplifying step indicates the presence of *C. hominis* in the sample. The method may further include the step of quantifying the amount of amplicons that is produced. This amount will be indicative of the amount of *Cryptosporidium* (e.g. *C. hominis*) in the sample. The method may be used, for example, to detect *Cryptosporidium* contamination in environmental samples such as water. In some embodiments, the sample may include several *Cryptosporidium* species other than *C. hominis*. In this case, the determining step permits discrimination between *C. hominis* and other *Cryptosporidium* species in the sample.

The invention further provides arrays for assessing the presence or expression of genes in *C. hominis*, and for detecting the interaction (e.g. binding) of *C. hominis* macromolecules. The array is a device comprising macromolecules such as nucleic acid probes, peptides, proteins, or antibodies, all of which originate from nucleic acid sequences of *C. hominis*, i.e. they are identical to or homologous to *C. hominis* genomic sequences; or are encoded by *C. hominis* genome sequences; or, in the case of antibodies, they bind to such macromolecules. In particular, the nucleic acid probes include nucleotide sequences homologous to nucleotide sequences of *C. hominis*. In one embodiment, the nucleic acid probes are at least 70 nucleotides in length.

BRIEF DESCRIPTION OF THE DRAWINGS

FIG. 1. Schematic representation of putative cellular components and metabolic pathways in *C. hominis*. The cytoplasmic membrane is indicated by a broad stripe at the top of the figure, and the intracellular compartment is below the stripe. Arrows and lines indicate pathways that are present. Dotted lines indicate multi-step reactions. Numbers indicate the quantity of transporters found for a given class when there is more than one. Important components or pathways that are clearly not present in *C. hominis* are crossed-out. Steps or components about which the exact nature is unknown or is questionable are shown with question marks. Arrows (⇛) and names indicate proposed aerobic parts of the energy metabolism. Abbreviations: ABC, ATP-binding cassette; MRP, multi-drug resistance protein; PEP, phosphoenolpyruvate; THF, tetrahydrofolate; DHF, dihydrofolate; AOX, alternative oxidase; UQ, ubiquinone; NADH DH, NADH dehydrogenase; Hsp70, heat-shock protein 70; Cpn60, chaperone 60; TIM17, translocase of the inner mitochondrial membrane 17; TOM40, translocase of the outer mitochondrial membrane 40; FAS, fatty-acid synthase; PKS, polyketide synthase; GPI, glycosylphosphatidylinositol; IP, inositol phosphate; PLC, phospholipase C; PKA, protein kinase A; PKC, protein kinase C; PI3K, phosphatidylinositol 3-kinase; AC, adenilate cyclase; Ado, adenosine; Cyd, cytidine; dThd, deoxythymidine; Urd, uridine; PNO-CPR, pyruvate:NADP+ oxidoreductase fused to cytochrome P450 reductase domain; Narf-like, nuclear prelamin A recognition factor like protein.

FIGS. 2A and B. A, typical amplification curve plots; B, standard curve plot of known amount of *C. hominis* rRNA.

DETAILED DESCRIPTION OF THE PREFERRED EMBODIMENTS OF THE INVENTION

The genetic sequence of the eight chromosome ~9.2 Mb genome of *C. hominis* has been determined and analyzed (see Table 1). By using genomics and bioinformatic approaches, a wide array of new targets for therapeutic and diagnostic applications has been identified. In addition, the overall metabolism of the organism has been elucidated, permitting a realistic approach to identification of critical points of attack (i.e. therapeutic targets) for therapeutics directed to the prevention or treatment of cryptosporidiosis. By "therapeutic target" we mean a molecule or pathway, the function of which can be targeted for intervention (e.g. blocking or inhibition) by the administration of agents such as drugs, or by stimulation of a specific immune response (by induction or passive administration (such as an antibody production. Such an intervention results in a decreased ability of the parasite to cause disease or disease symptoms. For example, such intervention may result in total or partial inhibition of the parasite's ability to carry out normal metabolism, to reproduce, to infect cells, to escape from infected cells, to proceed through a normal life cycle, to resist treatment with other disease alleviation agents, to navigate successfully, or to otherwise exert its pathological effects and cause disease.

In addition, *C. hominis* proteins that have been identified (or non-toxic or inactive fragments thereof) are useful for stimulating an immune system response to antigenic determinants of the proteins in an individual to whom they are administered. The nucleotide sequences and selected amino acid sequences of such proteins are provided in the Sequence Listing, the complete contents of which is hereby incorporated by reference. An immune system response may include increased antibody titers and/or increased cellular immunity, and, in a preferred embodiment, results in immunity to *C. hominis*. In other words, the proteins, or regions of the proteins encompassing antigenic determinants may be administered as vaccines for immuno prophylaxis. Alternatively, antibodies to antigenic determinants of the *C. hominis* proteins may also be administered directly to individuals in order to treat or prevent disease symptoms caused by *C. hominis*, i.e. immuno therapy. In addition, such antibodies may be useful as diagnostic or laboratory tools.

The highly tailored physiology of *C. hominis* suggests several potential therapeutic targets, examples of which include but are not limited to: 1) transport systems for peptides, amino acids, nucleosides, and sugars; 2) components of glycolysis; 3) the unique prokaryotic FAS1 (fatty acid synthase 1) and PKS1 (polyketide synthase 1); 4) starch and amylopectin biosynthesis or catabolism; 5) nucleic acid or amino acid metabolism; 6) the AOX (alternate oxidase) electron transport system; 7) the TS-DHFR (thymidine synthase-dihydrofolate reductase); and 8) the diverged polyamine synthesis enzymes. Importantly, and unlike other protozoan parasites, no extensive arrays of potentially variant surface proteins were observed, suggesting a possible role for immunoprophylaxis for prevention of cryptosporidiosis.

In addition, the invention provides the DNA sequences that encode numerous ribosomal RNA (rRNA) molecules (SEQ ID NOS: 4003-4014; see Table 14) and transfer RNA (tRNA) molecules (SEQ ID NOS: 4015-4059; see Table 13). These sequences are also provided in the Sequence Listing, the complete contents of which is hereby incorporated by reference. Those of skill in the art will recognize that rRNA and tRNA sequences may have many uses, including but not limited to: detection of *Cryptosporidium* in clinical samples, diagnosis of cryptosporidiosis in humans and animals, identification of *cryptosporidium* carriers, detection of *Cryptosporidium* in water supplies, detection of *Cryptosporidium* contamination in lakes, rivers or other environmental sites, etc. These targets, in particular the rRNA targets, are very useful for discrimination of *Cryptosporidium* strains; e.g., *C. hominis* and *C. parvum*. Finally, these targets are useful for quantification of *Cryptosporidium* in any of the above, or other, clinical, water or environmental samples. An example of this is shown in Example 6 below.

The practice of the present invention will employ, unless otherwise indicated, conventional techniques of molecular biology, microbiology, recombinant DNA, and immunology, which are within the skill of the art. Such techniques are explained fully in the literature eg. Sambrook *Molecular Cloning; A Laboratory Manual, Second Edition* (1989); *DNA Cloning, Volumes I and ii* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); *the Methods* in *Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology*, Volumes I-IV (D. M. Weir and C. C. Blackwell eds 1986).

Standard abbreviations for nucleotides and amino acids are used in this specification.

The present invention provides nucleic acid sequences from *Cryptosporidium hominis*, as provided in the Sequence Listing (and see Table 1). Those of skill in the art will recognize that such sequences may be used for a variety of purposes, including but not limited to translation of the amino acid sequences encoded therein, as probes for diagnostic assay for the detection of *C. hominis*, for expression in bacterial systems, for expression in fungal or insect cell systems, for generation of recombinant and subunit vaccines or immuno therapeutics, for generation of active enzymes, for purification for structural determination (e.g., standard biochemical and biophysical applications such as NMR, MS, XRay crystallography), for the construction of RNA and protein microarrays, for the construction of nucleic acid libraries, for comparative genome analysis, for phylogeny and taxonomy, for prediction of putative blocking peptide domains, etc. With respect to the nucleic acid sequences disclosed herein, those of skill in the art will recognize that many variants (derivatives) of the sequences may exist or be constructed which would still be suitable for use in the practice of the present invention. For example, with respect to the translation of amino acid sequences from the nucleic acid sequences, due to the redundancy of the genetic code, more than one codon may be used to code for an amino acid. Further, as described below, changes in the amino acid primary sequence may be desired, and this would necessitate changes in the encoding nucleic acid sequences. In addition, those of skill in the art will recognize that many variations of the nucleic acid sequences may be constructed for purposes related to other aspects of the invention, for example: for cloning strategies (e.g. the introduction of restriction enzyme cleavage sites for ease of manipulation of a sequence for insertion into a vector, for rendering the sequence compatible with the cloning system vector or host, for enabling fluorescent or affinity labeling technologies, etc.), for purposes of modifying transcription (e.g. the introduction of specific promoter or enhancer sequences, insertion or deletion of splice signals, for enhancing or negatively regulating transcription levels, for regulating polyadenylation, for controlling termination, and the like), or for modification of active or inactive domains, for elimination or modification of certain activities or domains, for optimizing expression due to codon usage or other compositional biases, for addition of immunologically relevant (enhancing or inhibiting) sequences or for any other suitable purpose. All such variants of the nucleic acid sequences disclosed herein are intended to be encompassed by the present invention, provided the sequences display identity in the range of about 50 to 100%, and preferably about 60 to 100%, or more preferably about 70 to 100%, or even more preferably about 80 to 100%, or most preferably about 90 to 100% or about 95 to 100% to the disclosed sequences. The identity is with reference to the portion of the nucleic acid sequence that corresponds to the original sequence, and is not intended to cover additional elements such as promoters, vector-derived sequences, restriction enzyme cleavage sites, etc. derived from other sources. Those of skill in the art are well-acquainted with methods to determine nucleic acid similarity or identity using simple software alignment tools such as FASTA, the BLAST suite of programs, CLUSTAW, Lineup, Pileup (GCG), or many others.

In addition, the nucleic acids of the present invention are not limited to DNA, but are intended to encompass other nucleic acids as well, such as RNA (e.g. mRNA, tRNA, rRNA, etc.), RNA-DNA hybrids, and various modified forms of DNA and RNA known to those of skill in the art. For example, for use in vivo, nucleic acids may be modified to resist degradation via structural modification (e.g. by the introduction of secondary structures, such as stem loops, or via phosphate backbone modifications, etc.). Alternatively, the nucleic acids may include phosphothioate or phosphodithioate rather than phosphodiesterase linkages within the backbone of the molecule, or methylphosphorothiate terminal linkages. Other variations include but are not limited to: nontraditional bases such as inosine and queosine; acetyl-, thio- and similarly modified forms of adenine, cytidine, guanine, thymine and uridine; stabilized nucleic acid molecules such as nonionic DNA analogs, alkyl- and aryl phosphonates; nucleic acid molecules which contain a diol, such as tetrahyleneglycol or hexaethyleneglycol, at either or both termini; etc. Further, the nucleic acid molecules may be either single or double stranded, or may comprise segments of both single and double strand nucleic acid.

The invention also provides vectors comprising nucleic acid sequences of the invention. Those of skill in the art are well-acquainted with various vectors that may be used e.g. for manipulation of nucleic acid sequences during genetic engineering procedures, for storage of stocks of the nucleic acid, for expression of an amino acid sequence encoded by the nucleic acid, for expression in bacterial, fungal, insect or other host systems, for delivery of DNA vaccines, for amplification of the DNA, for sequence analysis, for molecular interaction studies, etc. Many such vectors are known to those of skill in the art, and include but are not limited to plasmids, adenoviral vectors, various expression vectors (e.g. PTRIEX4, PET41, PET44, and others of the PET series, the pUC vector series, the BlueScript series, derivatives of pBR322 with ColE1 origin of replication, the TOPO vector series, the Gateway vectors, the TET repressor vectors, BAC vectors [pBeloBACs, pCC1BAC, etc.], pcDNA301 and related plasmids with the CMV promoter, pBAC insect vectors, pIEX for insect cells, and many others).

Many of the nucleotide sequences of the present invention represent open reading frames (ORFs) that encode for amino acid sequences, e.g. peptides, polypeptides, and proteins, all of which are also intended to be encompassed by the present invention. In general, for the purposes of the present invention, a peptide comprises about 15 or fewer amino acids, a polypeptide comprises from about 15 to about 100 amino acids, and a protein comprises about 100 or more amino acids, although the terms may be used interchangeably herein. The peptides, polypeptides and proteins of the present invention are generally provided as recombinant molecules, although the amino acid sequences may also be produced synthetically via known peptide synthesis techniques. The peptides, polypeptides and proteins of the present invention are provided in a substantially purified form, i.e. they are generally free of extraneous materials (such as other proteins, nucleic acids, lipids, cellular debris, etc.) and will generally be at least about 75% pure, preferably about 85% pure, and most preferably at least about 90-95% or more pure, as would be understood by one of ordinary skill in the art.

Importantly, the present invention comprehends all amino acid sequences that may be translated from the nucleic acid sequences of the present invention. In general, proteins/polypeptides that are so-translated will be translated from an open reading frame. The invention also encompasses variants (derivatives) of such proteins/polypeptides. For example, variants may exist or be constructed which display: conservative amino acid substitutions; non-conservative amino acid substitutions; truncation by, for example, deletion of amino acids at the amino or carboxy terminus, or internally within the molecule; or by addition of amino acids at the amino or carboxy terminus, or internally within the molecule (e.g. the addition of a histidine tag for purposes of facilitating protein isolation, the substitution of residues to alter solubility properties, the replacement of residues which comprise protease cleavage sites to eliminate cleavage and increase stability, the replacement of residues to form a convenient protease cleavage site, the addition or elimination of glycosylation sites, and the like, for any reason). Such variants may be naturally occurring (e.g. as the result of natural variations between species or between individuals, or as a result of different expression systems used to produce the amino acid sequence, etc.); or they may be purposefully introduced (e.g. in a laboratory setting using genetic engineering techniques). The amino acid sequences may be in a variety of forms, including a neutral (uncharged) forms, or forms which are salts, and may contain modifications such as glycosylation, side chain oxidation or deamidation, phosphorylation and the like. Also included are amino acid sequences modified by additional substituents such as glycosyl units, lipids, or inorganic ions such as phosphates, as well as modifications relating to chemical conversions or the chains, such as oxidation of sulfhydryl groups.

Strategies for improving solubility of cloned proteins are known to those of skill in the art. Such strategies may be used in the practice of this invention, and include: modifying expression conditions (temperature, buffer, nutrients), modification of the promoter or its activity, linking the protein to a different fusion protein that helps it maintain its solubility, expression in the yeast system *Pichia pastoris*, the insect baculovirus system, or in another eukaryotic organism, etc. Expression of soluble proteins is difficult in bacterial systems, but success is much more common in *Pichia*, baculovirus or mammalian expression systems.

All such variants of the sequences disclosed herein are intended to be encompassed by the teachings of the present invention, provided the variant protein/polypeptide displays sufficient identity to the original sequences, the original sequence being a sequence as disclosed herein, or an amino acid sequence that can be translated from a nucleic acid sequence disclosed herein, (e.g. from an ORF or portion thereof). Preferably, amino acid identity will be in the range of about 50 to 100%, and preferably about 60 to 100%, or more preferably about 70 to 100%, or even more preferably about 80 to 100%, or most preferably about 90 to 100%, or even 95 to 100%, of the disclosed sequences. The identity is with reference to the portion of the amino acid sequence that corresponds to the original amino acid sequence as translated directly from the nucleic acid sequences disclosed herein, i.e. not including additional elements that might be added, such as sequences added to form chimeric proteins, histidine tags, etc. Those of skill in the art are well acquainted with the methods available for determining the identity between amino acid sequences, for example, FASTA, FASTP, the BLAST suite of comparison software, ClustalW, Lineup, Pileup, or many other alignment software packages.

In addition, such protein/polypeptide variants retain at least about 50 to 100% or more of the activity of the original polypeptide, and preferably about 60 to 100% or more, or more preferably about 70 to 100% or more, or even more preferably about 80 to 100% or more, and most preferably about 90 to 100% or more of the activity of the original sequence. By "activity" we mean the activity or role of the amino acid sequence in *C. hominis*, which may include but is not limited to: enzymatic activity, activity as a structural component, activity as a transporter protein, activity in signal transduction, role as a membrane component, binding activity, activating activity, transport activity, etc.

In general, the amino acid sequences of the invention are produced in recombinant expression systems. In a preferred embodiment of the present invention, the recombinant system is an *E. coli* recombinant system, which can be expressed as well in mammalian cells for use, for example, as a DNA vaccine. However, the amino acid sequences may be produced in a variety of other recombinant expression systems. For example, yeast, insect cells (using for example, a baculovirus expression vector), plant cells (e.g. tobacco, potato, corn, etc.), transgenic animals, or mammalian cell culture systems can be used for expression of recombinant proteins. Any appropriate expression system that suitably produces the amino acid sequences of the invention may be used in the practice of the invention. Such systems and their use for the production of recombinant proteins are well known to those of ordinary skill in the art.

In some embodiments, vectors containing nucleic acid sequences (e.g. DNA) that encode the amino acid sequences of the invention will encode a single protein. However, this need not always be the case. Such vectors may contain DNA encoding more than one nucleic acid of the invention, either as separate, discrete sequences, or combined into a single chimeric sequence. For example, in the case of an expression vector, two or more nucleic acids according to the invention may be present in the vector, and the nucleic acids may be expressed separately, resulting in the translation of one amino acid sequence for each nucleic acid. Alternatively, a single polypeptide chain containing more than one amino acid sequence of the invention, or portions of more than one amino acid sequence of the invention, may be combined in tandem. For example, one or more highly antigenic proteins or regions of proteins of the invention may be expressed as a chimera from a single DNA sequence. Alternatively, the amino acid sequences of the invention may be expressed as part of a chimeric protein comprising amino acid sequences from another source, e.g. antigenic sequences known to be useful as adjuvants (e.g. PADRE [and other Pan-DR T helper cell epitope], hepatitis B core antigen, DNA sequences CPG, other chemokines, CTB or cholera toxin B subunit, Ricin B and other plant toxin subunits, LPS or lipopolysaccharide, KLH [key hole limpet hemocyanin], Freund's complete and Freund's incomplete adjuvant, and many other reagents, etc.), sequences that permit targeting of the protein to a specific location within the cell (e.g. nucleus, nucleolus or nuclear membrane, mitochondrion/mitosome/mitochondria-like organelle, membrane, endoplasmic reticulum, golgi, rhoptry, dense granules, calcisomes or acidocalcisomes, and other subcellular organelles compartments, etc.).

The invention also comprehends a cell or cells containing the nucleic acids and/or the amino acid sequences of the invention. For example, the cell may be a host cell that harbors one or more vectors containing nucleic acid sequences of the invention (e.g. DNA or RNA) and/or amino acid sequences of the invention translated from such vectors. Such cells may contain multiple vectors, and the vectors may be the same or different. Further, the cells may be either in vitro or in vivo.

The invention also provides antibodies directed to the amino acid sequences of the present invention. As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows binding of the antibody with the antigen. "Antibody" includes, for example, vertebrate antibodies, hybrid antibodies, chimeric antibodies, humanised antibodies, altered antibodies, univalent antibodies, Fab proteins and fragments, and single domain antibodies. Antibodies to the proteins of the invention, both polyclonal and monoclonal, may be prepared by conventional methods that are well-known to those of skill in the art. If desired, the antibodies (whether polyclonal or monoclonal) may also be labeled using conventional techniques.

Such antibodies may be used, for example, for affinity chromatography, immunoassays, and for distinguishing or identifying *C. hominis* proteins or portions thereof. In a preferred embodiment of the invention, such antibodies may be used therapeutically, e.g. for administration to patients suffering from cryptosporidiosis, or prophylactically in order to prevent cryptosporidiosis in patients at risk for developing the disease.

The invention also comprehends pharmaceutical compositions. The pharmaceutical compositions can comprise polypeptides, antibodies, or nucleic acids of the invention, or combinations of these. The pharmaceutical compositions will comprise a therapeutically effective amount of a polypeptide, antibody, or polynucleotide of the invention. The term "therapeutically effective amount" as used herein refers to an amount of a therapeutic agent that is sufficient to treat, ameliorate, or prevent a desired disease or condition, or to exhibit a detectable therapeutic or preventative effect. The effect can be detected by, for example, chemical markers or antigen levels. Therapeutic effects also include reduction of physical symptoms of cryptosporidiosis. The precise effective amount for a subject will depend upon several parameters, including the subject's size, general health, gender, age, etc., and the therapeutics or combination of therapeutics selected for administration. Thus, it is not useful to specify an exact effective amount in advance. However, the effective amount for a given situation can be determined by routine experimentation and is within the judgement of those of skill in the art, e.g. a physician. For purposes of the present invention, an effective dose will be from about 0.01 mg/kg to 50 mg/kg or about 0.05 mg/kg to about 10 mg/kg of active, therapeutic agent.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

In addition, pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Once formulated, the compositions of the invention can be administered to the subject. The subjects to be treated can be animals; in particular, human subjects can be treated. Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and intranasal, transdermal or transcutaneous applications (eg. see WO98/20734), needles, and gene guns or hyposprays. Dosage treatment may be a single dose schedule or a multiple dose schedule.

The present invention also encompasses vaccines that provide immunity to disease caused by *C. hominis*. By "immunity" we mean that administration of one or more proteins, polypeptides or peptides of the present invention to an individual either prevents the development of disease symptoms in that individual when exposed to or infected by *C. hominis*, or the disease symptoms that develop in the individual are milder than those that would otherwise develop, for example, the disease symptoms that would develop in a matched control individual. Those of skill in the art are well acquainted with the use and meaning of "controls" when comparing results of individuals or populations that have been exposed to different variables (e.g. vaccinated or not).

According to the invention, the vaccine may either be prophylactic (i.e. to prevent or attenuate symptoms of infection) or therapeutic (i.e. to treat disease after infection). Such vaccines comprise one or more of: immunizing antigen(s), immunogen(s), polypeptide(s), protein(s) and nucleic acid(s) from *C. hominis* (as described herein), usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogens. Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™ (WO 90/14837; Chapter 10 in *Vaccine design: the subunit and adjuvant approach*, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+ CWS (Detox™); (3) saponin adjuvants, such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor c[NF), etc; and (6) other substances that act as immunostimulating agents to enhance the effectiveness of the composition. Alum and MF59™ are preferred.

The immunogenic compositions (eg. the immunizing antigen/immunogen/polypeptide/protein/nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles. Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for eliciting the production of antibodies, for eliciting a cellular immune response, (or both), and/or for treatment or prevention of disease. This amount varies depending upon the health and physical condition of the individual to be treated, the taxonomic group of individual to be treated (e.g. nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials. The immunogenic compositions are conventionally administered parenterally, eg. by injection, either subcutaneously, intramuscularly, intranasally, or transdermally/transcutaneously. Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents. As an alternative to protein-based vaccines, DNA vaccination may be employed [eg. Robinson & Torres (1997) *Seminars in Immunology* 9:271-283; Donnelly et al. (1997) *Annu Rev Immunol* 15:617-648].

In a preferred embodiment of the invention, the proteins that are used in an immunogenic preparation or vaccine of the present invention include at least one of the proteins represented by SEQ ID NOS: 2, 4, 6, 8, 10, 12, 14, 16, 18, 20, 22 and 24 (see Example 2 below).

The present invention also provides tools and methods for the diagnosis of *C. hominis* infections. Such tools include primers containing nucleotide sequences that specifically hybridize to nucleic acid sequences that are unique to the genome of the *C. hominis* species. Hybridization of the primers to such a unique sequence permits amplification of the unique sequence (for example, by polymerase chain reaction (PCR)), thus providing a means to specifically identify the presence of *C. hominis* in biological samples (blood, feces, sputum, urine, bronchoaveolar lavage, etc.). Amplification may be directly from the genome of the organism located in the sample, or from RNA, e.g. from ribosomal RNA (rRNA), which is typically highly expressed and thus more sensitive than DNA as a target. Because the sequences that are amplified are unique to *C. hominis*, it is possible to distinguish infection by *C. hominis* from infection with even closely related parasites. By "primer" we mean a nucleotide sequence that hybridizes to another nucleotide sequence of interest, the primer typically being a relatively short nucleotide sequence (e.g. from about 10 to about 100 base pairs) and the nucleotide sequence of interest typically being transcribed from the genome of an organism. PCR amplification techniques are well-known to those of skill in the art In general, two primers are selected that target sites that flank the sequence of interest for diagnostics or identification. These primers are designed to recognize only the target sequence; i.e., they will hybridize only to the target sequence and to no other sequences. Thus, the sequence is screened against all other known sequences to ensure that there is no other known sequence to which it will hybridize. The primers generally range from 18-30 nucleotides in length (but can be longer or shorter), have Tm's (melting temperatures) that are selected to be compatible with both amplification conditions and with specificity, have little or no internal structure (stemloop structures caused by internal complementarity), little or not ability to dimerize with themselves, little or no ability to dimerize with the other primer, have few homopolymeric stretches, etc. Many computer programs (e.g., Primer3, Oligo, etc.) are available for these purposes. At times, an internal fluorescent probe is also included for specific use in even more sensitive and automated tests. The internal probe is fluorescently labeled such that it is specifically degraded and therefore fluoresces only if it specifically hybridizes to the target sequence. Alternately, other fluorescent probes can be designed that only fluoresce upon binding specifically to an amplified specific sequence. Thus, several alternative approaches are available for the generation and detection of specific sequences amplified by PCR, and any of these can be applied for diagnostic or identification purposes. (See, for example: Mullis, K., F. Faloona, S. Scharf, R. Saki, G. Horn, and H. Erlich. (1986) Specific enzymatic amplication of DNA in vitro: The Polymerase Chain Reaction. Cold Spring Harbor Symposia on Quantitative Biology 51: 263; Saiki, R. K., D. H. Gelfand, S. Stoffel, S. J. Scharf, R. Higuchi, G. T. Horn, K. B. Mullis, and H. A. Erlich. (1988) Primer-directed enzymatic amplification of DNA with a thermostable DNA polymerase. Science 239: 487; Schutzbank T E, Stern H J. (1993) Principles and applications of the polymerase chain reaction. J Int Fed Clin Chem. 1993 July; 5(3):96-105; Erlich H A. (1999) Principles and applications of the polymerase chain reaction. Rev Immunogenet. 1(2): 127-34; Wang, A. M., Doyle, M. V., and D. F. Mark. (1989) Quantitation of mRNA by the polymerase chain reaction. Proc Natl Acad Sci USA. 1989 December; 86(24): 9717-9721; Kawasaki, E. S., and A. M. Wang. (1989) Detection of gene expression. In: Erlich, H. A., ed., PCR Technology: Principles and Applications of DNA Amplification. Stockton Press, Inc., New York, N.Y., pp. 89-97; Dieter Klein (2002) Quantification using real-time PCR technology: applications and limitations. Trends in Molecular Medicine, 8(6):257-260; Buck G E. (1996) The polymerase chain reaction: a revolutionary new procedure for the laboratory diagnosis of infectious disease. J Ky Med. Assoc. April; 94(4):148-52.)

Because the nucleotide sequences that are being amplified are unique to C. hominis, a positive amplification result is indicative of the presence of C. hominis in the biological sample, and thus of infection by C. hominis. In contrast to current methods of C. hominis detection, the present invention, by elucidating the entire genome of C. hominis, allows the design of a much larger number of such primers. Further, primers provided by the present invention hybridize to sequences that are highly diverse from species closely related to C. hominis. Thus, the accuracy of the diagnostic methods of the present invention are superior to those of the prior art, resulting in very few false positives, and very few missed diagnoses.

The present invention also provides arrays of nucleotide or modified nucleotide, or protein or modified protein sequences, or antibodies to the nucleotides or proteins, for use as probes for assessing the presence or absence of genes, the expression of specific genes, the presence or absence of proteins or immune responses in *C. hominis* or other *Cryptosporidium* species. In particular, the arrays of the invention may be used to specifically assess the differential expression of genes any of the various stages of the life cycle of *C. hominis*, for example, during the sporozoite stage. In order to do so, a biological sample containing *C. hominis* parasites at a particular stage of development is provided and analyzed using the array. Alternatively, such arrays may be used to monitor *C. hominis* parasites under other conditions of interest, for example, to monitor gene expression in response to an external stimulus or variable, such as introduction of a drug or other agent into a culture of the parasites; or to monitor the course of a *C. hominis* infection, either in culture, or in an infected individual. Similarly, the arrays can be used for comparative genome analyses in which the presence or absence of specific genes are probed in different isolates of *Cryptosporidium*. In order to do so, DNA from the isolate of interest is analyzed using the array. Presence or absence of a particular gene is assessed via hybridization. Using this approach, the array can also be designed to detect specific polymorphisms in genes that have clinical or other relevance. This approach can have diagnostic and clinical importance, or other relevance to infection, treatment or contamination (e.g., water contamination with *C. hominis* is much more serious than water contamination with other species of *Cryptosporidium*. The nucleotide probes (usually DNA or a derivative thereof) in an array typically have a length in the range of about 50 to about 90 nucleotides, and preferably about 60 to about 80 nucleotides, and most preferably the probes have a length of about 70 nucleotides. These arrays can be comprehensive; i.e., be comprised of probes for all genes/gene sequences in a genome, or targeted to specific subsets of genes/gene sequences, depending on the application. Peptides, proteins or derivatives thereof (or antibodies thereto) can also be used in similar arrays. In this case, synthetic peptides, proteins (recombinant or otherwise) or derivatives are designed from the gene sequences (Table 1 and others) and used in the array. Again, these peptide/protein arrays can be of various lengths (number of amino acids or derivatives), and they can be comprehensive and include probes for all genes/proteins in the genome, or targeted to specific subsets of genes. These probes, nucleotides, peptides or derivatives thereof, are bound to solid phase surfaces (glass slides, microplates, micro- or nano-beads, etc.) and used to screen processed biological samples for interacting macromolecules. In the case of nucleotide arrays, interactions are usually detecting complementary sequences in a sample by hybridization. In the case of protein/peptide arrays, and in some cases for nucleotide arrays, the array will be used for detection of interacting macromolecules (proteins, antibodies, other nucleic acids, etc.).

EXAMPLES

Example 1

Herein, the ~9.2 Mb genome of *C. hominis* is described. The genome has 32% GC content, ~3,994 protein-coding genes, 45 tRNAs, and at least four rRNAs. There is a strikingly high concordance between the genome complement of *C. hominis* and the requirements imposed by the environmental niches it inhabits. Energy is derived largely from glycolysis and catabolism of starch or amylopectin. Options for both aerobic and anaerobic metabolism are available, the latter requiring an alternative electron transport system in a simplified mitochondrion. Biosynthesis capabilities are quite limited, but an extensive complement of transporters is encoded. Evidence of an apicoplast is absent, but rhoptry, microneme, dense granule, and acidocalcisome related genes are present. A panel of hypothetical signal transduction systems was identified. Comparison of the genomes of the human pathogen *C. hominis* and the bovine isolate *C. parvum* shows a high degree of synteny with no evidence of different gene complements. Phenotypic differences between these two parasites therefore seem to be due to very subtle sequence divergences.

The Genome Composition

A ~12 fold sequence and ~8 fold BAC clone coverage of the genome of *C. hominis* isolate TU502[1] is presented. Alignment[2] of these sequences with the HAPPY map[3] and chromosomes of the *C. parvum* genome[4] covered 9.1 Mb of the ~9.2 Mb. The eight chromosomes range from ~0.9-~1.4 Mb, and exhibit 31.7% GC content compared to 30.3% and 19.4% for *C. parvum* and *P. falciparum*[5]. The density of repeats of 2-50 bp was approximately one per 2800 bp. The distribution of repeats is biased toward chromosome ends as over 85% are in the telomere proximal thirds of five of the chromosomes. Two octamers, TGGCGCCA and TGCATGCA, over-represented in other apicomplexans[3], are ~40 and 15 fold over-represented in *C. hominis*. Interestingly, over 80% of the octamers are localized in non-coding sequences, suggesting a regulatory or other conserved function. 45 tRNAs, 4 or 5 rRNA operons—at least one of each of the two known types, and two clusters of three tandem 5S rRNA genes are present. Like *P. falciparum*[5], two methionine tRNAs are present, suggesting discrete roles in initiation and extension. We estimate 3,994 genes in *C. hominis*, compared to 3,952 genes in *C. parvum* and 5,268 in *P. falciparum* 5 (Table 2). Approximately 60% exhibit similarity to known genes. The distribution of GO annotations for *Cryptosporidium, Plasmodium*, and *Saccharomyces*, is remarkably similar, suggesting their phenotypic differences are a reflection of non-conserved or novel gene families of unknown function rather than to functional specialization of conserved gene families. Using ESTs as a guide, we estimate that 5-20% of *C. hominis* genes have introns.

Energy Metabolism.

*C. hominis* possesses a highly tailored glycolysis-based metabolism dependent on the host for nutrients and exquisitely adapted for its parasitic life cycle (see FIG. 1). Glycolytic enzymes are present, but the TCA cycle and oxidative phosphorylation (OxPhos) are not. Both an anaerobic pathway using pyruvate: NADP+ oxidoreductase (PNO) and an aerobic pathway using an alternative oxidase (AOX) are available for recycling NAD+ to NADH. In the former, pyruvate is fermented to acetyl-CoA producing NADPH which is then reduced to NADP+, releasing hydrogen, by a Narf like [FE]-hydrogenase, as for Trichomonas 6. Acetyl-CoA is processed by acetate CoAsynthase to produce acetate and ATP, as in Giardia[7], yielding four ATP per glucose.

Acetyl-CoA can also be processed to ethanol yielding no additional ATP. Under glucose-limited conditions, conversion of acetyl-CoA to acetate, generating two extra ATP per glucose, might be favored. In excess glucose, pyruvate can be converted to lactate or ethanol to regenerate NAD+ but no additional ATP. C. hominis can also generate ATP by metabolism of glycerol using glycerol-3-phosphate dehydrogenase and triose phosphate isomerase.

C. hominis can convert pyruvate to malate and subsequently to oxaloacetate (OAA), regenerating NAD+. However, malate shuttle enzymes (e.g., aspartate amino transferase) which process OAA to aspartic acid for export from the mitochondrion, are absent. We propose that cytoplasmic malate may be converted to OAA by a mitochondrial membrane bound malate dehydrogenase, like the lactate shuttle of Euglena gracilis[8], passing electrons from malate to an electron transport system comprised of elements of Complexes I and III and an alternative oxidase system (AOX) with $O_2$ as electron acceptor and producing no additional ATP.

Enzymes for metabolism of glycogen, starch and amylopectin are present, consistent with suggestions that amylopectin represents an energy reserve for sporozoites[9]. Lack of glucose-6-phosphate-1-dehydrogenase and other enzymes of the pentose phosphate pathway suggests that, unlike P. falciparum and other apicomplexans[10], C. hominis cannot metabolize five-carbon sugars or nucleotides. Components of beta-oxidation (e.g., enoyl-CoA hydratase and acetyl-CoA C-acyltransferase) are also absent, precluding ATP generation from fatty acids. Enzymes for catabolism of proteins are also absent. Major TCA cycle enzymes—isocitrate dehydrogenase, succinyl-CoA synthetase, succinate dehydrogenase—are absent in C. hominis. Despite the presence of ubiquinol-cytochrome C reductase, NADH dehydrogenase (ubiquinone), H(+)-transporting ATPase, iron-sulfur cluster-like proteins, etc., key components of Complexes II and IV are absent, precluding ATP generation by 0× Phos. Components of 0× Phos that are present (parts of Complexes I and III) probably re-oxidize NADH in a simplified electron-transport chain, as in some plants and protozoa[11].

Biosynthesis.

Consistent with previous suggestions (c.f. 12), Cryptosporidium lack enzymes for synthesis of key biochemical building blocks—simple sugars, amino acids and nucleotides. However, starch, amylopectin and fatty acids can be generated from precursors. Interestingly, these C. hominis enzymes exhibit minimal similarity to the known biosynthetic enzymes and therefore represent potential therapeutic targets.

Enzymes of the TCA, urea and nitrogen cycles, and the shikimate pathway are absent, suggesting that Cryptosporidium is an amino acid auxotroph. The shikimate pathway has been proposed as a potential target for glyphosate-based chemotherapy in other parasites including Cryptosporidium[13]. We found no evidence to support this hypothesis. Enzymes able to interconvert amino acids are encoded in C. hominis. However, unlike P. falciparum[5], C. hominis seems to have a full complement of amino acid transporters.

C. hominis lacks enzymes to synthesize bases or nucleosides, but encodes enzymes that convert nucleosides into nucleotides and interconvert nucleotides. As in other parasites, thymidylate synthase and dihydrofolate reductase (DHFR) of C. hominis are encoded as a bifunctional polypeptide, and novel polymorphisms at crucial sites have been proposed to explain Cryptosporidium's resistance to antifolates (c.f. 14). As previously suggested[12], several nucleotide conversion enzymes seem to have prokaryotic origin. Fatty acid biosynthesis in apicomplexans occurs in the apicoplast via a type II system including fatty acid synthase (FAS)[15]. However, consistent with absence of an apicoplast in Cryptosporidium[16], C. hominis encodes large FAS and polyketide synthase (PKS) enzymes, suggesting a type I mechanism (c.f. 17). As previously suggested[18], the type I FAS and PKS enzymes of C. hominis have prokaryotic characteristics.

Glycerolipid and phospholipid metabolic pathways for phosphatidylinositol (PI) biosynthesis are available in C. hominis. 1,2-diacylglycerol, an intermediate, is precursor for glycosylphosphatidylinositol (GPI) anchor synthesis. Consistent with previous observations 19, all enzymes required for synthesis of these anchors are encoded in the genome. Polyamines; e.g., putrescine, spermine and spermidine, are critical for cellular viability, and enzymes required for their synthesis are attractive therapeutic targets[20]. Cryptosporidium can synthesize polyamines using arginine decarboxylase rather than ornithine decarboxylase[21] The putative arginine decarboxylase, spermidine synthase and other relevant enzymes encoded by C. hominis are significantly diverged from their homologs and represent potential therapeutic targets.

Signaling and Control Pathways

C. hominis encodes adenylate cyclase, cAMP phosphodiesterase and protein kinase A, suggesting the presence of the cAMP-mediated signalling pathway (Tab.S7). Trimeric G protein, often involved in activation of cAMP mediated signalling, was not found in C. hominis, suggesting that, as for the Kinetoplastida[22] and reminiscent of plants, this pathway is independent of this complex in C. hominis. The presence of phosphatidylinositol 3-kinase and phospholipase C suggests that C. hominis utilizes phosphatidylinositol phosphate and $Ca^{2+}$-mediated regulatory mechanisms. The presence of putative $Ca^{2+}$ transporters, enzymes associated with acidocalcisomes, and calmodulin imply that $Ca^{2+}$ transport and sequestering are functional. Protein kinase C receptors suggest that C. hominis has the ability to signal by activation of soluble cytoplasmic receptor-associated kinases.

Organelles

No mitochondrial DNA sequences were found in C. hominis, and both the TCA cycle and OxPhos are absent. However, a double membrane bound organelle generates a proton gradient using cardiolipin and performs some related mitochondrial functions, and mitochondrial marker chaperonin[60] was localized to this structure[23]. Core enzymes of [Fe—S] cluster biosynthesis; i.e. CpFd1, IscU, IscS, mt-HSP70, mtFNR and frataxin, have been reported in Cryptosporidium[24], and we were not surprised to observe proteins involved in electron transport. We also used the CDART 25 to identify [Fe—S] domains in HscB (JAC) and ATM1, which are possibly involved in chaperonin activity of Hsp40/DnaJ type and ABC transport. Thus, C. hominis, like another obligate intracellular parasite, the microsporidian Encephalitozoon cuniculi[26], contains a minimal set of these proteins. These results imply significant mitochondrial function in C. hominis, and that the previously reported organelle[27] is an atypical mitochondrion.

Cryptosporidium apparently lacks an apicoplast[16,28], and searches of the C. hominis genome identified no clear apicoplast-encoded genes. Some putative nuclear-encoded apicoplast genes; e.g., *T. gondii* acetyl-CoA carboxylase 1 precursor[29], and *P. falciparum* adenylyl cyclase[30], are present. Others; such as the conserved apicoplast 50S ribosomal protein L33 of *Plasmodium*, the ribosomal L28 and S9 precursor[15] proteins of *Toxoplasma*, were not found. Together, our data suggest that *Cryptosporidium* lost an ancestral apicoplast. The presence of D-glucose-6-phosphate ketol-isomerase and 2-phospho-D-glycerate hydrolase that have highest similarity to plant genes and may be derived from ancient algal endosymbionts[31] is also suggestive that engulfment of the alga that gave rise to the apicoplast[32] preceded divergence of *Cryptosporidium* from other apicomplexans.

The *C. hominis* genome encodes multiple proteins specific for components of the apical complex including micronemes and rhoptries. No specific dense granule-associated proteins were observed, probably because these proteins diverge rapidly[33]. However, proteins implicated in the regulation of transport and enhancement of release of dense granule proteins[34] are present. As for *Plasmodium*, a typical Golgi structure is not apparent in *C. hominis* 28. However, the presence of secretory organelles implies the existence of a functional endoplasmic reticulum (ER) and Golgi, and *C. hominis* encodes proteins similar to many related components; including the NSF/SNAP/SNARE/Rab machinery which participates in dense granule release[35] and the rhoptry biogenesis mediator AP-1[36], involved in ER-Golgi-organelle protein traffic. Therefore, the ER-Golgi-organelle machinery of *C. hominis* is conserved and similar to that of other apicomplexans.

Transporters.

*C. hominis* exhibits very limited biosynthetic capabilities and is apparently supremely dependent on its ability to import essential nutrients. The genome encodes >80 genes with strong similarity to known transporters and several hundred genes with transporter-like properties. At least twelve sugar or nucleotide-sugar transporters, five putative amino acid transporters, three fatty acid transporters, 23 ABC family transporters including possible multiple drug resistance proteins[37], and several putative mitochondrial transporters are present. Other putative transporters for choline uptake, aminophospholipid transport, ATP/ADP transporters, and others with unclear function, were also identified. These transporters represent ideal therapeutic targets.

Comparison of *C. hominis* and *C. parvum* Genomes.

Comparison of the genomes of *C. hominis* and *C. parvum* showed that the two genomes are very similar; exhibiting only 3-5% sequence divergence with no large insertions, deletions or rearrangements evident. In fact, the gene complements of the two species are essentially identical since the few *C. parvum* genes not found in *C. hominis* are proximal to known sequence gaps. Thus, we conclude that the significant phenotypic differences between these parasites are due to functionally significant polymorphisms in relevant protein-coding genes and subtle gene regulatory differences.

Conclusions.

A striking feature of the *C. hominis* genome is the concordance between its gene complement and metabolic requirements in the environmental niches of its two primary life cycle stages—the quiescent oocyst in the nutrient-poor aerobic environment of contaminated water, and the vegetative parasites in the nutrient-rich anaerobic or microaerophilic environment of the host. Oocysts probably persist by processing stores of complex carbohydrates. Metabolism is likely aerobic via the alternative electron transport system in the unconventional mitochondrion. Consistent with the lack of an energy generating TCA cycle, OxPhos, β-oxidation, and the pentose phosphate pathway, oocysts are relatively inactive, and the two ATP per glucose from glycolysis may provide sufficient energy. In the host, the parasite can import sugars to directly fuel glycolysis, netting two ATP per hexose. In limiting glucose, an additional two ATP per hexose can be generated by converting acetyl-CoA to acetate or via glycerol metabolism. The residual mitochondrion lacks the TCA cycle and OxPhos as expected in an organism that replicates in the anaerobic/microaerophilic environments, and a simplified electron transport system for regenerating reducing power is available. Thus, a glycolysis-based metabolism is sufficient to support *Cryptosporidium* in all life cycle stages.

Also consistent with the highly tailored *Cryptosporidium* metabolism are its limited biosynthetic options; i.e., amino acids, nucleotides, and simple sugars cannot be synthesized. The parasite must import these building blocks probably explaining the significant array of transporters present in the genome.

As expected, apicoplast-specific activities are lacking in *Cryptosporidium*. One hypothesis is that acquisition of the type 1 FAS by a progenitor organism obviated the fatty acid synthesis capabilities of the apicoplast[38]. Since some apicoplast-related genes remain, our observations suggest that *Cryptosporidium* diverged from other apicomplexans prior to loss of this organelle.

As previously noted, our analysis shows that *Cryptosporidium* is a mosaic of sequences from diverse progenitors, including the hypothetical endosymbiont alga which formed the apicoplast, the mitochondrion, and numerous genes acquired from prokaryotes by lateral transfer. *Cryptosporidium* also exhibits modular gene loss. We assume, based on inference from other apicomplexans and earlier diverging groups like the Euglenozoa, the Heterolobosea, and the jakobids[39], that *Cryptosporidium* progenitors exhibited the TCA cycle, beta-oxidation, OxPhos, amino acid, nucleotide and sugar biosynthesis, fully competent mitochondria, and a functional apicoplast.

Genes associated with these functions are dispersed throughout the genome in *Plasmodium* and, we assume, in the progenitor. However, these systems seem to have been deleted cleanly in *Cryptosporidium*, leaving few residual genes or pseudogenes. Thus, its genome is a mosaic resulting from multiple lateral gene transfers and a complex pattern of selective gene deletion.

The highly tailored physiology of *C. hominis* suggests attractive therapeutic targets. Examples include: 1) transport systems for peptides, amino acids, nucleosides, and sugars, 2) components of glycolysis; 3) the unique prokaryotic FAS1 and PKS1; 4) starch and amylopectin biosynthesis or catabolism; 5) nucleic acid or amino acid metabolism; 6) the AOX electron transport system; 7) the TS-DHFR; and 8) the diverged polyamine synthesis enzymes. Finally, many potential vaccine targets were identified in the *C. hominis* genome (not shown), and unlike other protozoan parasites, no extensive arrays of potentially variant surface proteins were observed, suggesting a possible role for immunoprophylaxis for cryptosporidiosis.

The availability of the genome sequence of the human pathogen *C. hominis* represents a critical step forward in our understanding of the biology of this parasite. The gene complement provides very significant insight into its physiology and metabolism, validating previous hypotheses and suggesting others. New obvious targets for chemo- and immunotherapy are already apparent. In short, we anticipate that the availability of the sequence of *C. hominis* will stimulate very rapid progress in research on this organism, its pathogenicity, and strategies for intervention in the diseases it causes.

REFERENCES FOR EXAMPLE 1

1. Akiyoshi, D. E., Feng, X., Buckholt, M. A., Widmer, G. & Tzipori, S. Genetic analysis of a *Cryptosporidium parvum* human genotype 1 isolate passaged through different host species. *Infect. Immun.* 70, 5670-5675 (2002).
2. Gordon, D., Abajian, C. & Green, P. Consed: a graphical tool for sequence finishing. *Genome Res.* 8, 195-202 (1998).
3. Bankier, A. T. et al. Integrated mapping, chromosomal sequencing and sequence analysis of *Cryptosporidium parvum*. *Genome Res.* 13, 1787-1799 (2003).
4. Abrahamsen, M. S. et al. Complete genome sequence of the apicomplexan, *Cryptosporidium parvum*. *Science* 304, 441-445 (2004).
5. Gardner, M. J. et al. Genome sequence of the human malaria parasite *Plasmodium alciparum*. *Nature* 419, 498-511 (2002).
6. Muller, M. Evolutionary relationships among Protozoa. Coombs, G. H., Vickerman, K., Sleigh, M. A. & Warren, A. (eds.), pp. 109-131 (Kluwer Academic Publishers, 1998).
7. Sanchez, L. B., Galperin, M. Y. & Muller, M. Acetyl-CoA synthetase from the amitochondriate eukaryote *Giardia lamblia* belongs to the newly recognized superfamily of acyl-CoA synthetases (Nucleoside diphosphate-forming). *J. Biol. Chem.* 275, 5794-5803 (2000).
8. Jasso-Chavez, R. & Moreno-Sanchez, R. Cytosol-mitochondria transfer of reducing equivalents by a lactate shuttle in heterotrophic Euglena. *Eur. J. Biochem.* 270, 4942-4951 (2003).
9. Petry, F. & Harris, J. R. Ultrastructure, fractionation and biochemical analysis of *Cryptosporidium parvum* sporozoites. *Int. J. Parasitol.* 29, 1249-1260 (1999).
10. Barrett, M. P. The pentose phosphate pathway and parasitic protozoa. *Parasitol Today* 13, 11-16 (1997).
11. Nihei, C., Fukai, Y. & Kita, K. Trypanosome alternative oxidase as a target of chemotherapy. *Biochim. Biophys. Acta* 1587, 234-239 (2002).
12. Striepen, B. et al. Gene transfer in the evolution of parasite nucleotide biosynthesis. *Proc. Natl. Acad. Sci. U. S. A* 101, 3154-3159 (2004).
13. Roberts, C. W. et al. The shikimate pathway and its branches in apicomplexan parasites. *J. Infect. Dis.* 185 Suppl 1, S25-S36 (2002).
14. Atreya, C. E. & Anderson, K. S. Kinetic characterization of bifunctional thymidylate synthase-dihydrofolate reductase (TS-DBFR) from *Cryptosporidium hominis*: A paradigm shift for TS activity and channeling behavior. *J. Biol. Chem.* (2004).
15. Waller, R. F. et al. Nuclear-encoded proteins target to the plastid in *Toxoplasma gondii* and *Plasmodium falciparum*. *Proc. Natl. Acad. Sci. U. S. A* 95, 12352-12357 (1998).
16. Zhu, G., Marchewka, M. J. & Keithly, J. S. *Cryptosporidium parvum* appears to lack a plastid genome. *Microbiology* 146 (Pt 2), 315-321 (2000).
17. Zhu, G. et al. Expression and functional characterization of a giant Type I fatty acid synthase (CpFAS1) gene from *Cryptosporidium parvum*. *Mol. Biochem. Parasitol.* 134, 127-135 (2004).
18. Zhu, G., Marchewka, M. J., Woods, K. M., Upton, S. J. & Keithly, J. S. Molecular analysis of a Type I fatty acid synthase in *Cryptosporidium parvum*. *Mol. Biochem. Parasitol.* 105, 253-260 (2000).
19. Priest, J. W., Xie, L. T., Arrowood, M. J. & Lammie, P. J. The immunodominant 17-kDa antigen from *Cryptosporidium parvum* is glycosylphosphatidylinositol-anchored. *Mol. Biochem. Parasitol.* 113, 117-126 (2001).
20. Bacchi, C. J. & Yarlett, N. in *Biochemistry and Molecular Biology of Parasites*. Marr, J. J. & Müller, M. (eds.), pp. 119-131 (Academic Press, New York, 1995).
21. Keithly, J. S. et al. Polyamine biosynthesis in *Cryptosporidium parvum* and its implications for chemotherapy. *Mol. Biochem. Parasitol.* 88, 35-42 (1997).
22. Parsons, M. & Ruben, L. Pathways involved in environmental sensing in trypanosomatids. *Parasitol. Today* 16, 56-62 (2000).
23. Crawford, M. J., Fraunholz, M. J. & Roos, D. S. in *Molecular Medical Parasitology*. Marr, J. J., Nilsen, T. W. & Komuniecki, R. W. (eds.), pp. 154-169 (Academic Press, New York, 2003).
24. LaGier, M. J., Tachezy, J., Stejskal, F., Kutisova, K. & Keithly, J. S. Mitochondrial-type iron-sulfur cluster biosynthesis genes (IscS and IscU) in the apicomplexan *Cryptosporidium parvum*. *Microbiology* 149, 3519-3530 (2003).
25. Geer, L. Y., Domrachev, M., Lipman, D. J. & Bryant, S. H. CDART: protein homology by domain architecture. *Genome Res.* 12, 1619-1623 (2002).
26. Katinka, M. D. et al. Genome sequence and gene compaction of the eukaryote parasite *Encephalitozoon cuniculi*. *Nature* 414, 450-453 (2001).
27. Riordan, C. E., Ault, J. G., Langreth, S. G. & Keithly, J. S. *Cryptosporidium parvum* Cpn60 targets a relict organelle. *Curr. Genet.* 44, 138-147 (2003).
28. Tetley, L., Brown, S. M., McDonald, V. & Coombs, G. H. Ultrastructural analysis of the sporozoite of *Cryptosporidium parvum*. *Microbiology* 144 (Pt 12), 3249-3255 (1998).
29. Zuther, E., Johnson, J. J., Haselkorn, R, McLeod, R. & Gornicki, P. Growth of *Toxoplasma gondii* is inhibited by aryloxyphenoxypropionate herbicides targeting acetyl-CoA carboxylase. *Proc. Natl. Acad. Sci. U. S. A* 96, 13387-13392 (1999).
30. Muhia, D. K. et al. Multiple splice variants encode a novel adenylyl cyclase of possible plastid origin expressed in the sexual stage of the malaria parasite *Plasmodium falciparum*. *J. Biol. Chem.* 278, 22014-22022 (2003).
31. Dzierszinski, F. et al. The protozoan parasite *Toxoplasma gondii* expresses two functional plant-like glycolytic enzymes. Implications for evolutionary origin of apicomplexans. *J. Biol. Chem.* 274, 24888-24895 (1999).
32. Fast, N. M., Kissinger, J. C., Roos, D. S. & Keeling, P. J. Nuclear-encoded, plastid-targeted genes suggest a single common origin for apicomplexan and dinoflagellate plastids. *Mol. Biol. Evol.* 18, 418-426 (2001).
33. Beyer, T. V., Svezhova, N. V., Radchenko, A. I. & Sidorenko, N. V. Parasitophorous vacuole: morphofunctional diversity in different coccidian genera (a short insight into the problem). *Cell Biol Int.* 26, 861-871 (2002).
34. Stedman, T. T., Sussmann, A. R. & Joiner, K. A. *Toxoplasma gondii* Rab6 mediates a retrograde pathway for sorting of constitutively secreted proteins to the Golgi complex. *J. Biol. Chem.* 278, 5433-5443 (2003).
35. Chaturvedi, S. et al Constitutive calcium-independent release of *Toxoplasma gondii* dense granules occurs through the NSF/SNAP/SNARE/Rab machinery. *J. Biol. Chem.* 274, 2424-2431 (1999).
36. Ngo, H. M. et al. AP-1 in *Toxoplasma gondii* mediates biogenesis of the rhoptry secretory organelle from a post-Golgi compartment. *J. Biol. Chem.* 278, 5343-5352 (2003).
37. Zapata, F., Perkins, M. E., Riojas, Y. A., Wu, T. W. & Le Blancq, S. M. The *Cryptosporidium parvum* ABC protein family. *Mol. Biochem. Parasitol.* 120, 157-161 (2002).

38. Zhu, G. et al. *Cryptosporidium parvum*: the first protist known to encode a putative polyketide synthase. *Gene* 298, 79-89 (2002).
39. Simpson, A. G. et al. Evolutionary history of "early-diverging" eukaryotes: the excavate taxon *Carpediemonas* is a close relative of *Giardia*. *Mol. Biol. Evol.* 19, 1782-1791 (2002).

Example 2

Identification of Categories of Genes and Proteins of *C. hominis*

Introduction

Genomic sequences from pathogenic microorganisms provide fundamentally new approaches for development of vaccines and chemotherapeutic agents. Thus, reverse vaccinology invokes bioinformatics analyses to identify potential candidates from the genome data by "in silico" analysis. This approach has been successfully applied to identify putative vaccine candidates from bacterial genomes that traditional vaccine development methods have not detected. This approach (see Scarsellie et al, 2005, for review) has recently been applied in several bacterial systems including for example group B streptococci and *Neisseria meningitidis*. See, for example, the following references: 1) Maione D, Margarit I, Rinaudo C D, Masignani V, Mora M, Scarselli M, Tettelin H, Brettoni C, Iacobini E T, Rosini R, D'Agostino N, Miorin L, Buccato S, Mariani M, Galli G, Nogarotto R, Nardi Dei V, Vegni F, Fraser C, Mancuso G, Teti G, Madoff L C, Paoletti L C, Rappuoli R, Kasper D L, Telford J L, Grandi G. Identification of a universal Group B *streptococcus* vaccine by multiple genome screen. *Science.* 2005 Jul. 1; 309(5731): 148-50; 2) Scarselli M, Giuliani M M, Adu-Bobie J, Pizza M, Rappuoli R. The impact of genomics on vaccine design. Trends Biotechnol. 2005 February; 23(2):84-91; 3) Serruto D, Adu-Bobie J, Capecchi B, Rappuoli R, Pizza M, Masignani V. Biotechnology and vaccines: application of functional genomics to *Neisseria meningitidis* and other bacterial pathogens. J. Biotechnol. 2004 Sep. 30; 113(1-3):15-32. Review; 4) Kurz S, Hubner C, Aepinus C, Theiss S, Guckenberger M, Panzner U, Weber J, Frosch M, Dietrich G. Transcriptome-based antigen identification for *Neisseria meningitidis*. Vaccine. 2003 Jan. 30; 21(7-8):768-75; and, 5) Pizza M, Scarlato V, Masignani V, Giuliani M M, Arico B, Comanducci M, Jennings G T, Baldi L, Bartolini E, Capecchi B, Galeotti C L, Luzzi E, Manetti R, Marchetti E, Mora M, Nuti S, Ratti G, Santini L, Savino S, Scarselli M, Storni E, Zuo P, Broeker M, Hundt E, Knapp B, Blair E, Mason T, Tettelin H, Hood D W, Jeffries A C, Saunders N J, Granoff D M, Venter J C, Moxon E R, Grandi G, Rappuoli R. Identification of vaccine candidates against serogroup B *meningococcus* by whole-genome sequencing. Science. 2000 Mar. 10; 287(5459):1816-20.

Similarly, systems wide analyses of these pathogens using genomic data leads to identification of potential 'weak links' or 'Achille's Heels' in the biological processes of the pathogen, which can be exploited for the development of inhibitors of processes essential to the parasite. Gene expression and proteomic technologies complement the "in silico" analysis of the genome data to identify potential vaccine and chemotherapeutic targets. Similar approaches lead to the identification of new biomarkers for the detection of these pathogens and diagnosis of disease caused by them.

*C. hominis* genes of several types that are of great potential as chemo- or immuno-therapeutics, immuno-prophylactics, and/or detection/diagnostics/quantification agents, have been identified. These genes fall into several general classes: 1) transporters; 2) receptors; 3) surface and secreted proteins; 4) organellar proteins; 5) signal transduction proteins and kinases; 6) critical metabolic enzymes; and 7) specifies specific sequence differences. The application for each of these is outlined briefly below.

Transporters. *C. hominis* lacks genes and consequently the enzymes and metabolic pathways required for several essential functions: e.g. biosynthesis of simple sugars, amino acids, nucleotides, fatty acids, etc. Thus, these important pathogens are dependent on their environment or host for these essential compounds, and these compounds must be transported across the parasite's membrane by a host of essential transporters. A list of these transporters is given in Table 3.

Knowledge of the sequence of these transporter genes and consequently the protein sequences permits us to predict their functions and to some degree their cellular locations and structures. Specific knowledge of the function of a transporter; e.g., a nucleotide-sugar transporter, provides a means to block the activity of that molecule. Blocking the activity of an essential transporter will prevent the parasite from importing essential compounds and the parasite will die. Thus, these transporters represent ideal targets for chemotherapeutic development.

Similarly, transporters must function at the host-parasite interface; i.e., the parasite membrane exposed to the extracellular domain. This exposed location makes these molecules ideal targets for immunoprophylaxis or immunotherapy. Vaccines developed against these proteins could: 1) protect relevant human populations or animal populations; 2) provide a means to treat infections. Thus, active or passive immunization against pools of these proteins could: 1) prevent infection; 2) provide a therapy for the cryptosporidiosis. The therapeutic effect could result from: 1) killing the parasite via normal immune mechanisms activated by immunization; 2) blocking the activity of the molecule via immune mechanisms and thereby starving the parasite until it is cleared by normal mechanisms. Thus, transporters are ideal targets for vaccines, and could be used for both immuno-prophylaxis and immuno-therapy.

Receptors. Receptors are essential for cell-cell signalling, sensing of the environment, host parasite interactions, uptake of essential nutrients, etc. Receptors by definition are located on the membrane surface in some contact with the extracellular environment. A list of *C. hominis* receptors is given in Table 4. Blocking of the function of these macromolecules would likely be lethal to the parasite. The extracellular location of these receptors renders them available for attack by the host or passive immune mechanisms, and available for chemotherapeutics unable to cross most membranes. Thus, receptors are excellent targets for immuno-prophylaxis and therapy, or chemotherapy.

Surface and secreted proteins. There are many parasite proteins associated with the surface of the cell, and some that are secreted into the extracellular milieu. A list of over 1000 *C. hominis* proteins that are associated with the membrane or secreted is given in Table 5. Receptors and transporters will also be members of this group of proteins. Independent of the actual function of these macromolecules, they are amenable to attack by the host immune system or by passive immunization. Thus, these molecules are also idea targets for active or passive immuno-therapy or prophylaxis.

Organellar proteins. *C. hominis* is a member of the Apicomplexan parasites, and therefore encodes genes that generate apical complex organelles responsible for invasion and pathogenesis of the parasites, and other organelles required for its survival. A list of genes which are involved in organellar biosynthesis and function is given in Table 6. Since these organelles, systems and enzymes are specific to these parasites, they represent ideal targets for therapeutics.

Signal transduction proteins and kinases. These proteins are required for proper, responsive and sensitive gene regulation in the parasite. Lacking the function of these proteins and enzymes, the parasites are unable to respond to their environment properly, or to differentiate correctly. Therefore, these enzymes are required for the viability of this parasite and thereby represent ideal targets for therapeutic (chemo- or immuno-) attack. A list of these proteins and enzymes is given in Table 7.

Critical metabolic enzymes. As outlined above, we have developed a fairly comprehensive understanding of the metabolism of *Cryptosporidium* simply by analysis of the genes encoded in its genome. Thus, we can see that the parasite is highly dependent on glycolysis for energy, for amino acid interconversion for generation of amino acids, for fatty acid biosynthesis and degradation, for nucleotide synthesis. Blockage or inhibition of these processes would likely be lethal for the parasite. A list of such essential metabolic enzymes and proteins is given in Table 8. These enzymes represent ideal targets for specific chemotherapeutics.

Species specific sequence differences. We now know nearly the entire genome sequence of *C. hominis*. Thus, we can now easily compare all of its genes to those of related parasites and pathogens. DNA/RNA of these genes provide very specific and easily readable signatures, and these signatures are generally species-specific. Thus, we have identified many sequences that can be useful for identifying *C. hominis*, and discriminating this parasite from other microbes (Table 9). These signature sequences can also be used for detection, quanitification and diagnostics, as well as for chemotherapeutic targets.

The *C. hominis* genes disclosed herein and the proteins they encode are newly discovered and have not been used as targets for possible immunotherapeutic purposes, or as targets for chemotherapeutic agents, or as tools for detection/diagnosis of the parasites. As outlined above, there is no immuno- or chemotherapy available for *C. hominis*. It is essential to develop such therapies. The newly identified genes and the proteins they encode provide a new approach to chemo- and/or immunotherapy. Their advantages include one or more of the following:
1. they are essential for viability of the parasite
2. they are localized on the surface of the parasite
3. they should be accessible to the host immune system or to blocking agents
4. much is known about these processes (e.g., transport, metabolism, etc.) and analogs that block them can be designed
5. the proteins/peptides thereof can be synthesized chemically or in recombinant bacteria
6. the peptides differ significantly from host molecules (both host and parasite homologs have been fully sequenced), and analogs that block the parasite version can be designed so that they do not block any host function.
7. vaccinogens can be designed so that the host immune response will act only on the parasite protein.

In short, these new genes present novel targets for chemo- and immunotherapy and prophylaxis for Cryptosporidiosis, a disease for which no such agents currently exist. Genome Annotation. The DNA sequence of *C. hominis* was annotated using a suite of analysis programs to identify important genes. Protein genes and their structural and functional annotations were derived. Approximately 4,000 genes were identified Table 1). Similarly, structural RNA genes (tRNA, rRNA) were identified (not shown).

Vaccinology.

One focus of research in the *Cryptosporidium* vaccinology project has been application of "in silico" genome analysis to identify potential vaccine candidates from the complete genome sequence of *Cryptosporidium hominis*. The general steps that are followed are:
1. Apply bioinformatics tools to predict possible antigens from the whole genomic sequence.
2. Focus searches for possible antigens by gene expression analysis, proteomics, and other "systems" approaches.
3. Clone, express, and purify putative candidates.
4. Validate the possible protective or biological role of the candidates in animal and "in vitro" models.
5. Select antigens with positive results for further testing in animals and eventually in humans.

Reverse Vaccinology in *Cryptosporidium*

Identification of potential target antigens using bioinformatics: The initial step was to apply bioinformatic tools to scan the whole genome sequence of *C. hominis* focusing on proteins that are predicted to be secreted, ER localized, surface-exposed and/or contain antigenic motifs, and that therefore represent potential vaccine targets. Since these proteins are most likely to be exposed to the immune system, they constitute the initial target of the project. This approach has been successfully used for several ne recombinant vaccines (see, for example, Scarsellie et al, 2005, fore review.) Screening of the genome has been carried out using various programs that predict the following characteristics:
   presence of a signal peptide
   possible membrane protein by presence of transmembrane domains
   GPI—anchor domains
   antigenicity
   similarity to virulence factors characterized in other pathogens
   no similarity to human proteins.
   role in transport of ions or essential metabolitesions or essential metabolites.

Using various bioinformatics tools, close to 500 *Cryptosporidium* candidate proteins that are most likely exposed to the immune system were identified (Table 10). Priority is given to those that present a single transmembrane domain, as those are less likely to be toxic to *E. coli* or other vector hosts used for cloning and expression of the recombinant proteins.

Focus Searches Using Gene Expression and Proteomics

The best antigens for vaccines are likely to be those associated with the membrane during sporozoite stages in the development of the parasite. The sporozoite form of the parasite is responsible for invasion of the intestinal epithelium causing pathology. To identify those proteins, a microarray that targets every gene in the *C. hominis* genome has been generated. The arrays are used to identify those genes that are expressed in *C. hominis* sporozoites. These arrays detect mRNAs transcribed from the genes. Therefore, in parallel with the gene expression array work, proteomics analyses are performed. A database containing all *C. hominis* proteins has been constructed, and *C. hominis* oocysts and sporozoites are analyzed for those proteins that are expressed in those stages of the parasite. This information permits identification of proteins for vaccinogens.

The array in its current configuration consists of ~4,000 70 base synthetic oligonucleotides bound to glass slides. Each of the ~4,000 *C. hominis* genes is represented by a single, specific oligonucleotide in the array. In order to assess expression of these genes in a specific stage, a biological sample containing C. hominis parasites at that stage of development is provided. Total RNA is isolated by standard technology, labeled with fluorescent dyes, and hybridized to the array. A similar RNA sample derived from an alternative stage of the parasite's life cycle is used is labeled with an alternative fluorescent dye and used as a control. Both labeled RNAs are hybridized to the same oligonucleotide array, and the arrays are washed and scanned in a fluorescence scanner. The readout of the scanner provides an estimate of the amount of RNA for each gene that is present in the initial sample and a comparison between the two samples provides an estimate of the relative expression level of each gene in the two samples. Thus, genes that are up or down regulated relative to the control can be identified.

In addition to examining gene expression differences in various life cycle stages, these arrays may be used to monitor C. hominis parasites under other conditions of interest, for example, to monitor gene expression in response to an external stimulus or variable, such as introduction of a drug or other agent into a culture of the parasites; or to monitor the course of a C. hominis infection, either in culture, or in an infected individual.

The 70 base oligonucleotides in the array were designed by ArrayOligoSelector™ version 3.8.2, (http://arrayoligosel-.sourceforge.net/), which selects optimal sequences by:

1. Examining every possible 70 mer sequence from every gene;
2. Using BLASTN (against the whole genome) to check the uniqueness of each 70 mer.
3. Uniqueness is scored as the theoretical binding energy of a candidate oligo to its most similar genome sequence. The binding energy is calculated using a nearest-neighbour model with the established thermodynamic parameters;
4. Using the LZW compression algorithm to calculate the sequence complexity score in bytes between the oligo sequence and the its compressed version;
5. Determining the self-annealing score, calculated as the alignment score of the optimum local alignment between the oligo sequence and its reverse compliment using the Smith-Waterman algorithm;
6. Calculating the GC content of the oligo;
7. Choosing, for each gene, the oligo that maximizes uniqueness and sequence complexity, minimizes self-annealing and has GC content closest to specified by the user; also tries to minimize distance to the 3' end of the gene.

The oligos were synthesized commercially and validated in the lab, and the process is ongoing. Initial tests were performed as follows:

The oligos were reconstituted to 100 pmoles with sterile distilled water;

Several dilutions (10, 25 and 50 pmoles) were tested for the best printing conditions;

Two test plates were printed on Corning UltraGAPS slides (amino-silane coated);

These slides were stained in SYBR Green II and hybridized with Cy-dye labeled RNAs.

The results of the initial prints indicated that the oligos were intact and the hybrodization was strong. The relatively even staining indicated that that hybridization of each gene was essentially equivalent. Finally, lack of hybridization to the negative control confirms specificity of the hybridization. Thus, use of the array to identify genes that are expressed in *C. hominis* sporozoites by detecting transcribed mRNAs was validated.

Cloning and Expression of Protein Candidates in *Escherichia coli*

In parallel with the gene expression array work, proteomics analyses have also been performed. A database containing all *C. hominis* proteins has been constructed, and *C. hominis* oocysts and sporozoites are characterized for those proteins that are expressed in those stages of the parasite. This information permits us to focus on the most likely proteins for vaccinogens.

The cloning and expression of the candidates has been carried out using the pET system from Novagen that allows the cloning of PCR products in a ligase-independent reaction (Ek/LIC cloning). The proteins of interest are expressed as fusion proteins to an epitope tag that permits their detection and purification. Various tags (e.g. His-Tag, GST-tag and Nus-Tag, etc.) are known and available. In addition the Ek/LIC cloning system can be adapted and used in a high throughput pipeline for the cloning and expression of recombinant proteins.

The cloning of PCR products by LIC requires the presence of non-complementary single-stranded overhangs in the vector that anneal to complementary single stranded overhangs on the PCR fragment. In order to create these overhangs the LIC method uses the 3'-5' exonuclease activity of T4 DNA polymerase, which in the presence of a single deoxyribonucleotide creates very specific 13-14 base single stranded overhangs in both vector and PCR fragment. The primers used in the PCR reaction include 5' extensions that after the treatment with T4 DNA polymerase generate the overhangs complementary in the fragment to the overhangs created in the vector.

```
Sense primer:
                                          (SEQ ID NO: 4001)
5' GAC GAC GAC AAG ATX-insert specific sequence 3'

Antisense primer:
                                          (SEQ ID NO: 4002)
5' GAG GAG AAG CCC GGT-insert specific sequence 3'
```

After treatment with T4 DNA polymerase in the presence of dATP the PCR fragment is flanked by the overhangs as shown below:

```
                                          (SEQ ID NO: 4001)
     5' GACGACGACAAGATX-Target protein-xxA (SEQ ID NO: 4002)
     AX-Target protein-xxTGGCCCGAAGAGGAG 3'
```

As a first step, the genes encoding thirteen of these antigens were PCR amplified from genomic DNA. The PCR products were purified and cloned into the vector pTriEX-4, a vector that allows the expression of the proteins as 6X-His and S-tag fusion products in both prokaryotic and eukaryotic hosts. The His-tagged products can be purified through nickel-activated columns. The recombinant plasmids were characterized by restriction enzyme analysis and DNA sequencing to confirm the presence of the *Cryptosporidium* target gene. Protein overexpression: The recombinant plasmids were used to transform the *Escherichia coli* strain BL21 (DE3) or other appropriate vector for expression of the fusion proteins. The target genes are cloned into pTriEX-4 under the control of the bacteriophage T7 promoter. Transcription is initiated by the enzyme T7 RNA polymerase which is present in the chromosome of the bacterial host and is under the control of an inducible promoter. In the presence of the inductor, IPTG, T7 RNA polymerase is produced in the bacterial host resulting in the expression of the target protein. This gives this system an excellent way to regulate the production of the target protein under controlled conditions, which is a point to consider in case that the protein has a toxic effect in *E. coli*. The level of expression is very high and can be 50% of the total protein present in the bacterial host. The expression of the recombinant genes was carried out by culturing bacteria in 3 ml of Overnight Express Instant Tb medium (Novagen) at 37° C. for 12-13 hours. This medium is designed to achieve a high level of expression with IPTG-inducible bacterial systems without the need of monitor cell growth. Expression has been achieved for all but the Zn++ transporter and the Thrombospondin-containing gene TSP1. The Zn transporter seems to be toxic for *E. coli* as bacterial cultures containing the Zn-transporter clones start to lyse after they reach early stationary phase. Most of the proteins were expressed in *E. coli* in an insoluble form as inclusion bodies. The exception is the gene encoding the Profilin-like protein.

Therefore, these proteins were expressed using a different vector since the same PCR product can be cloned in different vectors. Two additional epitope tags were assayed, GST and NUS. The proteins expressed from clones in the GST-tag vector were also insoluble. The proteins obtained from the NUS-tag expressed the protein in higher amount compared to the previous two vectors and the fusion proteins can be detected in the soluble fraction by Western blot. Very high levels of expression have been achieved with the Nus-tag clones which results in proteins becoming soluble as detected by gel staining. The results for the experiments are summarized in Table 11.

The nucleotide sequences that encode the proteins, and amino acid sequences of the proteins, are as follows:

1) Zinc transporter (Chro.10338, start position 677, end position 2053) is encoded by the nucleotide sequence:

```
                                                  (SEQ ID NO: 1)
ATGAAAGACTCAGGTCTGGAAAAGCCATTACTTAATGGGAATGGATTTAA

AATATTTGCAAGTACAGAGAGTGTTCAGAAGAGGTTAATATATGCAATCT

TTTTCTGTCTAGTCTTTACATTGATAGAGGTTGTTGTGGGTATATTATCA

AACTCACTGGCACTAATATCAGATGCATCTCACCTCATTTCAGATATATG

TAGCTATTTCATTTCTCTGCTTGGTATCCACCTTTCCAAAAGAAAGGCCA

CAAACACAATGTCATTTGGTTATAACAGAGCTGAAATATTAGGGGCTTTG

TTAAGCATTCTACTAATATGGTTCATGACAATCATGCTTGTTTACGAGGC

TATTCAAAGAATGTTATATCCTGTGAATGTTGATGGGTTTTCTATGTTTA

TTACCGCTATTTTTGGTACTTTGTCCAACTTATTTATTAGCTTTGTGTTA

TCTGTTCACAATCATGGAATAGGTTCAATTGGAGCAGATTGTACCCAACA

CAATCATACACATGAACATATGCATGAACACGACTGTAAGCAAGCTCAAA

CTCATTTTCAGGATGATTCACTGTATTGCAAAGATCAACAACTAGTAGAA

AATCAAGAACAAATTGGAGGAATTAACACTACTTTACTTGAATACCACCA

TAGAAGCCAAATGAGAACTAAGGATTTAGATCATGAACTTAATAATTATA

CTAATTTAATGAACTCTCCAGTTATAAGAAGAGTCAATTCTGGTTTAAAA

GAGTGTTCAGAACGTCAAAATGACTATTCTCATCTCCATAGTAATAATCA

CTATCCAAGTAAACATTCCTCTGAACAAGAAAGCTTAGCGCTTAAGTCTG
```

-continued
```
CTTATATCCATGTTTTAGGGGATATTTTACAGAACATCGGAGTAATGATT

GCTGGATTACTGATTTTATACAATCCAGCATGGACAATCGCCGATCCTCT

ATGTACTATTCTATTCTCCTTCTTTGTCCTCGCAACAACCATCAAAATCC

TAAAAGATTCCGCCAATGTTCTAATGGAAGGAGCCCCTATAGGAATTGAT

TGTGAATCCATTCAAAACGACTTTCTAAAGCTTTCTTCAGTGCTTGAAGT

TCACGATCTACATGTTTGGTCTGTATCTGTTGGAGTTCCTGCATTATCTT

GTCATATTGTCGTAGCATCAGAAGATAATGCTAGATTTACATTAAGATAT

GCAACGGATCTCTGTCAAAAGAAATATGGAATATTTCACACCACCATTCA

AATTGACTATTCTCCAAATAAAGCCACTTGTGAAACAATACATCATCAAA

AATGTCTAGTTGGCTCTAATAACCAAAATAAAAGTGAAATTCACCAAATA

ATTCATCCCGTTGACTATTCTGCTTAG
``` and has amino acid sequence:

```
                                                  (SEQ ID NO. 2)
MKDSGLEKPLLNGNGFKIFASTESVQKRLIYAIFFCLVFTLIEVVVGILS

NSLALISDASHLISDICSYFISLLGIHLSKRKATNTMSFGYNRAEILGAL

LSILLIWFMTIMLVYEAIQRMLYPVNVDGFSMFITAIFGTLSNLFISFVL

SVHNHGIGSIGADCTQHNHTHEHMHEHDCKQAQTHFQDDSLYCKDQQLVE

NQEQIGGINTTLLEYHHRSQMRTKDLDHELNNYTNLMNSPVIRRVNSGLK

ECSERQNDYSHLHSNNHYPSKHSSEQESLALKSAYIHVLGDILQNIGVMI

AGLLILYNPAWTIADPLCTILFSFFVLATTIKILKDSANVLMEGAPIGID

CESIQNDFLKLSSVLEVHDLHVWSVSVGVPALSCHIVVASEDNARFTLRY

ATDLCQKKYGIFHTTIQIDYSPNKATCETIHHQKCLVGSNNQNKSEIHQI

IHPVDYSA;
```

2) Ribosomal protein S19 (CP15) (Chro.60368, start position 13760, end position 14197) is encoded by the nucleotide sequence:

```
                                                  (SEQ ID NO. 3)
ATGGCAGATACTGAACAAAAGAAGAGAACCTTCAGAACTTATAGTTACAG

AGGTGTTGACCTCGACAAGCTCCTTACCATGAAATTGGATGAGGTTGTTG

AGCTTTTACCAGCACGTAAAAGACGTAAGATAGCCAGAGGTTGTCTTAAC

AGAAGAACTGCAGCTTTTATCGCAAAGCTTCGCAAATCTAAGGCTGAATG

TCCAATGGGTGAGAAACCTGTTGCTGTTCGTACCCATTTACGTAATATGG

TTATCCTCCCAGAAATGGTTGGTTCTGTTGCAGGTGTCTACAATGGTAAG

ACTTATGTTACCGTTGAAATTAAGCCAGAAATGATTGGGATGTACCTTGG

AGAGTTCTCTATCACCTACAAGCCAGTACGTCATGGTAAGCCAGGTGTTG

GTTCAACCAGTTCTTCCAGATTCATTCCTCTAAAGTAA
``` and has amino acid sequence:

```
                                                  (SEQ ID NO. 4)
MADTEQKKRTFRTYSYRGVDLDKLLTMKLDEVVELLPARKRRKIARGCLN

RRTAAFIAKLRKSKAECPMGEKPVAVRTHLRNMVILPEMVGSVAGVYNGK

TYVTVEIKPEMIGMYLGEFSITYKPVRHGKPGVGSTSSSRFIPLK;
```

53) Mucin-like glycoprotein 900 (Chro.70447, start position 855, end position 3963) is encoded by the nucleotide sequence:

(SEQ ID NO. 5)
ATGACAACAACAACAACACCACCATTACCTGATATCGGTGACATTGAAAT
TACACCAATCCCAATTGAAAAGATGTTGGATAAGTATACAAGAATGATTT
ATGACTATAACAGTGGTTTATTATTAGACTCTAATGATGAACCAATTCCA
GGTTCTCAAGCAGGACAAATAGCTGATACAAGCAATTTATTCCCAACTCA
AACTCACAAGAGTACTGGTTTACCAATTGATCCAATGGTTGGTCTTCCAT
TTGATCCAAAATCAGGTAATTTAGTACATCCATATACCAATCAAACAATG
TCTGGTTTATCAGTATCATATCTTGCTGCTAAGAATTTGACAGTTGATAC
TGATGAAACCTACGGTTTACCAATTGATACACTCACTGGTTACCCATTAG
ATCCAGTTAGTTTGATTCCATTCAATCCAGAAACTGGTGAATTGTTTGAT
CCAATCTCAGATGAGATCATGAATGGAACAATTGCAGGTATTGTTTCAGG
AATTTCTGCAAGTGAGTCATTATTATCTCAGAAATCAGCTCAAATCGACC
CAGCAACAAATATGGTTGTTGGCGAATTTGGTGGATTGTTGAACCCAGCA
ACAGGAGTGATGATTCCAGGTTCTTTAGGTCCATCAGAGCAAACTCCATT
CTCCCCTGAAATTGAAGATGGTGGTATTATTCCTCCAGAAGTAGCAGCAG
CAAATGCTGATAAATTCAAGTTATCTATTCCTCCAAGCGTACCAGAATCA
ATTCCAGAAAAGGATCAGAAGATCGATTCTATTTCTGAATTGATGTATGA
TATTGAGTCAGGTAGACTTATTGGTCAAGTATCAAAGAGACCAATCCCAG
GTTCAATTGCTGGTGATTTGAACCCAATAATGAAGACACCAACACAAACT
GACAGTGTAACTGGTAAGCCAATCGATCCAACCACAGGTTTACCTTTCAA
TCCACCAACTGGTCATTTGATTAACCCAACAAATAATAATACCATGGATT
CTTCATTTGCTGGTGCATACAAATATGCAGTTTCAAATGGTATCAAGACT
GATAATGTTTATGGTTTACCAGTTGATGAAATAACAGGTTTGCCAAAGGA
TCCAGTCTCAGATATTCCATTTAACTCAACTACAGGTGAATTGGTTGATC
CATCAACAGGAAAGCCAATTGACAATTCTACTGCTGGTATTATTAGTGGA
AAACCTGGCTTACCACCTATTAAAGATGAAAATGGCAATTTGTTTGATCC
ATCAACTAACTTGCCAATAGATGGTAATAACCAATTAATTAACCCAGAAA
CCAACAGTACTGTCCCAGGATCAACTTCAGGTTACTACAAAACCAAAGCC
AGGAATTCCAGTCAATGGTGGAGGTGTTGTACCTAATGAAGAAGCTAAAG
ATCAAGCTGATAAGGGTAAGGATGGATTAATTGTTCCACCAACTAATTCT
ATCAATAAGGATCCAGTAACAAATGCTCAATACAGTAATAGTACTGGTAA
CATTATTAACCCAGAAACAGGAAAAGTTATTCCAGGCTCACTTCCAGGCT
CTCTCAACTATCCATCATTCAATACTCCACAACAAACTGATGAGATTACA
GGAAAGCCAGTTGATACTGTTACTGGTTTGCCATATGATCCATCTACAGG
TGAAATTATCGATCCAGCAACTAAATTACCAATTCCAGGATCGGTTGCAG
GTGATGAAATTCTCACTGAAGTATTGAACATTACAACAGATGAAGTAACA
GGTTTGCCAATTGATCCTGAAACCGGTCTTCCAAGAGATCCAGTATCAGG
ACTCCCACAACTTCCAAATGGTACTTTGGTTGATCCATCAAATAAAAAAC
CAATTCCAGGTTCACATTCTGGATTTATTAATGGTACATCTGGAGAACAA

TCACACGAGAAAGATCCAGGTACTGGTAAGCCACTTGATCCAAATACAGG
TTTACCATTCGATGAAGATTCTGGTAGTTTAATTAACCCAGAGACTGGAG
ATAAACTTCAAGGATCACATTCTGGTACATTTATGCCAGTGCCAGGTAAG
CCACAAGGTGAAAATGGAGGTATCATGACACCTGAGCAGATATTGGAAGC
ATTAAATAAATTGCCAACAAGTAATGAAGCAAAATATTTCACCAAAACCA
AGTTCAGATGCTGTTCCAGACAAACCAACAAATACTTGGTGGAATAAGAT
TTCTGGTCAAACCTACCAGGTTGATGGAGAGAAGACTATTCCAGGTTCTG
CAGCTTCAGTAATTCACACTGCTCTTGGAACACCAACTCAAACTGATCCA
ACAACAGGACTTCCATCTGATCCATCAACAGGTTTACCATTCATTCCAGG
ATTTAACGTACTTGTAGATCCTCAGACTGGAGAGCAAATGAAGGGTTCTG
TTCCTTATGTTTCATTGTACGTTAAGGAAAAGAACATTGTAACAGAAGCT
GCTTATGGTCTACCAGTTGATCCAAAGACTGGTTTCCCAATTGATCCAAT
TAGTTACCTCCCATTTGCTAAGAATGGTGAATTAATTGATCCTATCTCTG
GTAAATATTTCAGTGGTTCAATTGCTGGATTCATTTCTGGTAAAGCTGGT
ACACAATCTAAATCATCTGATGAGTCAGGTAATCCAATTGATCCATCAAC
AAATATGCCTTACGATCCAAAAACAGGCAAATTAATTGATCCAGAATCTG
GCATTGCTATTGATAATTCTATTTCAGGTGTATTTGCAACTGTACCTGGT
ACTGCTGCACCGAAAAAGGGTGGTGTCATTCCAGAGTCAGTTGCAGCTGA
GGCAGCAAAGAAATACTTTGCAGCCAATGTTGAAGGAGGAGAAGGAGAAA
AAGTTCCACCACCACCAGAATCATCTAGTAACATTGCAATCCAAGCTGCT
GGTGGTGCTTCTGCTGCTGTAGGTCTCGTAGCTGCTGGTGTTGGTGCATG
GTATGCAAGCAGAAACAGACAAGAAGGAGAAGATGATGATGACTATGCAG
ATGGATTTGAAGCAGAATATGAAGAAGAAGAGGAAGAAGAGGGTGATGAA
GCAGCAAATGAAACTGTTGTTACAATTGAGCGTGATTCATCATTCTGGAA
CGAATCTTAA and has amino acid sequence:

(SEQ ID NO. 6)
MTTTTTPPLPDIGDIEITPIPIEKMLDKYTRMIYDYNSGLLLLDSNDEPIP
GSQAGQIADTSNLFPTQTHKSTGLPIDPMVGLPFDPKSGNLVHPYTNQTM
SGLSVSYLAAKNLTVDTDETYGLPIDTLTGYPLDPVSLIPFNPETGELFD
PISDEIMNGTIAGIVSGISASESLLSQKSAQIDPATNMVVGEFGGLLNPA
TGVMIPGSLGPSEQTPFSPEIEDGGIIPPEVAAANADKFKLSIPPSVPES
IPEKDQKIDSISELMYDIESGRLIGQVSKRPIPGSIAGDLNPIMKTPTQT
DSVTGKPIDPTTGLPFNPPTGHLINPTNNNTMDSSFAGAYKYAVSNGIKT
DNVYGLPVDEITGLPKDPVSDIPFNSTTGELVDPSTGKPIDNSTAGIISG
KPGLPPIKDENGNLFDPSTNLPIDGNNQLINPETNSTVPGSTSGTTKPKP
GIPVNGGGVVPNEEAKDQADKGKDGLIVPPTNSINKDPVTNAQYSNSTGN
IINPETGKVIPGSLPGSLNYPSFNTPQQTDEITGKPVDTVTGLPYDPSTG
EIIDPATKLPIPGSVAGDEILTEVLNITTDEVTGLPIDPETGLPRDPVSG
LPQLPNGTLVDPSNKKPIPGSHSGFINGTSGEQSHEKDPGTGKPLDPNTG

-continued

LPFDEDSGSLINPETGDKLQGSHSGTFMPVPGKPQGENGGIMTPEQILEA

LNKLPTSNEAKYFTKTKFRCCSRQTNKYLVEMKQNISPKPSSDAVPDKPT

NTWWNKISGQTYQVDGEKTIPGSAASVIHTALGTPTQTDPTTGLPSDPST

GLPFIPGFNVLVDPQTGEQMKGSVPYVSLYVKEKNIVTEAAYGLPVDPKT

GFPIDPISYLPFAKNGELIDPISGKYFSGSIAGFISGKAGTQSKSSDESG

NPIDPSTNMPYDPKTGKLIDPESGIAIDNSISGVFATVPGTAAPKKGGVI

PESVAAEAAKKYFAANVEGGEGEKVPPPPESSSNIAIQAAGGASAAVGLV

AAGVGAWYASRNRQEGEDDDDYADGFEAEYEEEEEEEGDEAANETVVTIE

RDSSFWNES;

4) CP15/60 (Chro.40225, start position 10793, end position 12259) is encoded by the nucleotide sequence:

(SEQ ID NO. 7)
ATGTTCGAGTTTATTTCAGAAATGTTTCATTCATGTTGCAAATTAAAAAA

AAATCAAAGAATGATGAATACATTTTTATCTTGTGCCCTACCCCAAGTG

ATTTAGAAGAGGAATATATTGATCAAGAAGGAAATGTCAAAAAAAGAAG

CTCGAAAAAATTAGAGGAACTGCCAGAAATATTGTCGATAAGGAAATTGT

CAGGGAGTGGAGTGGAAGGGAAATTGGAAGCTGTATTTGCTGTCATTTAA

TATATGAAGACGAAATGAATGTTTATAGAGCTGATAAATATGGCAGACAT

ATTGGTAAGGACCATGAAGAATATGAAGGTAGCCAAACAAGAGAAGAAAA

CCGTGTTAACTCAGTTGAATCTCTGAGCTCATATGGCTCAAGAAAACATT

TTTCTGAGGAGCCAAATAGCGCAGATTCCAACTCTACCTCAATAAGTTCA

GATGAAAATAATAATGCAGTTGAGAATAAGAGTAAAAAAACAAGAGAAAG

GAGGAAGTTAAATATCAGTAGATCCCCAAGCGTAATTGAGAAGGAAATAG

ATGAAAAAGAAAAGAAGAACAAAAAACTAAAAGAAACAAAAGATGCCAAT

AATAAAGAATGCTCCACAATTAGTTCTGATATAAATAATGATATCCATAA

CGCGGATGAGAAAACAACTGATAATAGAAATAACAAAAAGCTAGAGAATA

CTAATGTAAAGAATGACGAGCAAATTCCATTCTCCGATCAAAAAAAATAT

TCTAAATCTTCTCCACTCTCAAAGAATCAATGCCCTCCAAAGTTAGGAAA

AAGGCCACCCATGAAGAATGAATTATTGGCTATGAATGGTCAGAAAAACA

ATTCACTTAAGTCATCAATTGCAAATAGTAAAAAAATGTAGTAAAAAAATA

TCAAGTACTCCGAAAAATGAATTTAACAAAATAATTTTGGAAAAAGAAAA

GGTAGAAAGTAATTCTCGCGATACTCATAAAGATGACAAAAATCAAACTG

GAAATAATAATGACCAGCAAATCAACCACATTACTAGCAGTTCTAATTCT

GATAAAGAAATGATTGATAACAGTGGGGAATTAAATATGAAGAGGAAGA

GATGAAGTTTAACAAAGATATTTCTTCGAAAATAATACGTCACAGAGCAT

TAATAGGAATTCAAGCCGAAATTATTCTAAAAGATGGATCGACAACGGAC

TGTAAAGTTAGCTTCTCAGATGAGGAAGATGATCTTTCATTTATTTGCAA

CGATAAAGTTAAAGCTGTTCCTTGGAGTAACATTAAAGAGATTTTTACAA

CAAAAAGTGAACTTAGAATGGTGAATACACGAGCACCTATTTTTAAAGAC

CCAACATTAATTATTGCACTACATTTAAAAGATACAGGAAATTGTATACC

TTTGAAATTTGATTCTAAGAAAAGCAAAGAAGATTTTTTAAATTTCGCCC

TCAGAATGATTGGGTAA and has amino acid sequence:

(SEQ D NO. 8)
MFEFISEMPHSCCKLKKNQKNDEYIFILCPTPSDLEEEYIDQEGNVKKKK

LEKIRTARNIVDKEIVREWSGREIGSCICCHLIYEDEMNVYRADKYGRHI

GKDHEEYEGSQTREENRVNSVESLSSYGSRKHFSEEPNSADSNSTSISSD

ENNNAVENKSKKTRERRKLNISRSPSVIEKEDEKEKKNKKLKETKDANNK

ECSTISSDINNDIHNADEKTTDNRNNKKLENTNVKNDEQIPFSDQKKYSK

SSPLSKNQCPPKLGKRPPMKNELLAMNGQKNNSLKSSIANSKKCSKKISS

TPKNEFNKIILEKEKVESNSRDTHKDDKNQTGNNNDQQINHITSSSNSDK

EMIDNSGEIKYEEEEMKFNKDISSKIIRALIGIQAEIILKDGSTTDCKVS

FSDEEDDLSFICNDKVKAVPWSNIKEIFTTKSELRMVNTRAPIFKDPTLI

IALHLKDTGNCIPLKFDSKKSKLEDFLNFALRMIG

5) Thrombospondin related adhesive protein (TRAP C1) (Chro.10390, start position 4021, end position 6078) is encoded by the nucleotide sequence:

(SEQ ID NO. 9)
ATGAAAAAGTTAATACTTTATTTAGTATTACTACATATATATATTGTTCA

GAAATATGTAATATGTTCAAAATTAACTCATTATTCAGTAGGTGGTCATG

CATCAACATCAAGAGTGAAGGGAAGAAGTAGTAGTGGTAGTAGTAGTAGT

AGTGGCGATTTTAATGTACCAGGATTAAATGGATATTTATGTCCAAGCTA

TAATAGAGACCCAAGAGGATTTGGTTGTTTTGGTATGAATACAGCATATA

CGGTTAAAAAGAATAGTTGGCAAGAATGTGCAAATCAATGCTATTGGAGT

AAATATACAGTATTTGGTAATTGTCAAAGATCTGTATATAATTCAAATAA

TAAAGATTGCTATATTAAAAGTGGTGATAACAGATGCGTGAAGTCTCCAG

ATGGAATGATTTTAACAAATAGGCAATCATATATGATCGGAGAGTGTGCG

ACAACATGTACTGTTTCAACTTGGTCAAGTTGGACTACATGCTCAGGGGT

ATGTGGTGAGATGAGATCAAGAACAAGAAGTGTGTTATCATTTCCAAGAT

ACGATTATGAATATTGTCCACATCTGATAGAGTATTCAAATTGTGTAGTA

CAAAATAAATGCCCAGAAAATTGCCCACAGTATGGGGTTTCAATATTGGG

ATGGGGATGTCAGTTTGAATCAACTTTTTCATTTAATAAAAATTTATTTG

TTAGTTATGAAGAAGATTGGAGGGGTTGCATGTCAACTTGCAAACAGGAT

CCATTTTGTGTAGCTTGGTCGTATAATGCAACTTTATCAGAAGGACCAGA

TTCTGTTGGATTTTCAAGAGAATATCGTCCATGTTATACACATAGATTTG

CTTCAGGATGTCAAGCTTTAGCACCAGGATGGGTATCAGGTAATAAGAAT

ACAATAAATGTTGATTGTGAAACTGGTACTTGTATACATAATGAATGGTC

ATCTTGGACAACATGTAAAGATCCTTGTAGTAATACTGAAACAATGAGTA

GAAATAGGACAGTAAAGACTGTATCTCAGAATTGGGCAAGTACACCTTGT

AGGGATGAGACTCAAATTCAACTTTGTTCAGAAAACCCACAAAGTATTGA

AACTTGTAAAACTTGTTTAGTAGGTGGTTGGTCAGAATGGTCAGATTGTT

-continued

```
CAACAAGTTGTGGAGAAGGTAATAGAGTTAGAACACGTGAAGTTACTAAA
CCTCCATTGAATGGAGATGATTCAACATGCCCAGAATTAATTGAGAAAGA
AAGTTGTAATAAAGATGTGGAATGTCCACATGTTCAATGTGATTGGGAGA
ATGGTCTTCTTGGTCACCTTGTAGTGTAACTTGTGGATGCGGAACAACTA
CAAGAAATAGGGAAGTAAAGGGAGAGAATTGTACAGAATTATCAACAGAA
TCAAAGAAGTGTAATTTGGCAAATTGTGACGATAACTCTGCATCATGTAC
TGCAGTTATGTCAGTTTGGTCAGAATGGTCAGTTTGTAGTGAGAAATGTG
ATCAGGGAGTAGTAAGAAGGTATCGTGATTTTGATTTTACAAAAATTGGG
GTTTTTGGTTATAATCCACCCGGTACATCAGAAGAACAAAATAAAGTGAG
AGAAATATGCAAGGATACTCCAACATTAGAAGAGGAGCCATGTACTTCAG
GAGTTGCATGTACTCCAGGATGTAAATATACTGAATGGAGTACTTGGTCA
AGCTGTGATTGTTCTGGAACTCAAACTAGAGATAGAGTTGTTACTTTCCC
TGAAGGTGTAATTGATGCAACTTGTCAGAGTTCTAAAGATACAAGATCAT
GTAGCAAGCCTGAAGGTTGTACAGAAACTGCTCCAGATTCTGGAGACGCT
ACACTTGCCATTGCTATTGGATTACCAGTTGGTATTCTTGGATTATGCAT
TATTGCTGGTTCTTTGTTTTTAATTGGTGGGAGATCAGGTGATCAGGAGG
AGGATGAGACAAGTTATCAATACTTTGATCAACCTTCTGCTACTTTAGAT
CAAGACTCAGAATATGTTCAAGAAATTGGTCCAGAGAGTCAGAACTGGGC
TAGTTGA
``` and has amino acid sequence:

```
                                        (SEQ ID NO. 10)
MKKLILYLVLLHIYIVQKYVICSKLTHYSVGGHASTSRVKGRSSSGSSSS
SGDFNVPGLNGYLCPSYNRDPRGFGCFGMNTAYTVKKNSWQECANQCYWS
KYTVFGNCQRSVYNSNNKDCYIKSGDNRCVKSPDGMILTNRQSYMIGECA
TTCTVSTWSSWTTCSGVCGEMRSRTRSVLSFPRYDYEYCPHLIEYSNCVV
QNKCPENCPQYGVSILGWGCQFESTFSFNKNLFVSYEEDWRGCMSTCKQD
PFCVAWSYNATLSEGPDSVGFSREYRPCYTHRFASGCQALAPGWVSGNKN
TINVDCETGTCIHNEWSSWTTCKPCSNTETMSRNRTVKTVSQNWASTPCR
DETQIQLCSENPQSIETCKTCLVGGWSWSDCSTSCGEGNRVRTREVTKPP
LNGDDSTCPELIEKESCNKDVECPHVQCELGEWSSWSPCSVTCGCGTTTR
NREVKGENCTELSTESKKCNLANCDDNSASCTAVMSVWSEWSVCSEKCDQ
GVVRRYRDFDFTKIGVFGYNPPGTSEEQNKVREICKDT
```

6) TSP1 domain-containing protein TSP7 precursor (Chrom 60103, start position 12, end position 1982) is encoded by the nucleotide sequence:

```
                                        (SEQ ID NO. 11)
ATGGATTCAATTAACTTTAGAAGCATTTATATTCCATCAGCAGTGAGGTA
TATTATATTACTTTTATTATGGACAATATTTACAAAAAATGTTTATAGTG
AAAGTAGTGAAGAAACTTTATTGGGAAGATCAGTATTGGATTTAAACAAG
AAAAATACATGTGAATACTATGGAGAGCAGGATGGTATGTTTACTGATTC
ATTTCATTCAAGAATATGTATAGTTCCAGAAGATGGATTACATGGAAAAA
GGGAATATGAAAATCATCAAAAAAAAACATTTGGAACAATTAGACCAAAT
AATAAACAATTATCTGATAATAAATTATATAGGAAAGATGATGATTTAAC
TTCTTCAATTGCAGATTTTGATAGTAATTCTGTGAGAATACAGAGAAAAA
ACGTGGATTTAGAAGCTATGTTTGGAATAGGAAAAGATAACAACAGAATG
AATCTTAATAATGAAGCAATTCAAAGTTTCTATTCAAATAATGAAACAGA
AAGCCAAGATAAGAATGCGACAAACGACTATTTTTTATTTAAAGAAGGAC
TTTTGAAATTTCAAGAGAAAAAGATATTAAGATATTATTTATATGATGTA
GGAAATAAAGTCTATTCAGATACTATAGCTTATCCAGAAAATGTTATATC
AGAAAACTGTGCATTTAACTATTTGGGGAATTATGTAGATGTTTATGAAA
TTAGTAAAGTATCAGATCCACCAGTAATTTCATGGCCAAATAATCACATA
GTTTTTATACACTCTCAGGTAAAATCTGATGGTACATTTAAATTTCAAGT
ATATACTAGCTCAGGAGAGATAGGATTTTATTTTGAAGTAACTGATAATA
GTTATAAAACAGGTTGTGGTAGTTATTCTAGAGTTGATAAAAGCAAATTT
ACTCACTCTGCAAATTCTTTAATTCAAGTTCAATTAGTAAGAAGAAAGTT
TGGATTTAATGTATTTGTTGATGGTACTAGAAGAACACAACTAGATATAA
TTGATTGTATTGCAAGTGTTCCAACTAAAGTTCAAATAACTAGTGGATCA
GGATCACAAATTTATCCAAAAGTAGAAGATTGTCAAATTTCACAGTGGAC
AGATTGGTCAACTTGTTCAAAAACTTGCTCAACTGGTTCAAAAGCTAGAT
ACCGTTCAGTAATTATGCCAAGTATGAATGGTGGTTTACCATGTCCTAAA
TTACTTGATTCAAGTCCTTGTAATGCTGATATTTCATGCTCATCATGCCA
ATATTCGGAATGGACAATGTGGGGTGAGTGCTCAGCTACTTGTGGATCAG
GATCAACAACCAGAACAAGAAAGTTATTAAGTGCAGCATATTTTATTGAA
AGCTGTATTGATACATTCCAATTAAAATCTTGCCATGGTGTTTCTTGCGC
TAGTGATTGTATTGTAACAGAATGGTCAGATTGGAGCGAATGTAGTACAA
CTTGCGGTGTTGGAAGTCAAATTTCCACAAGATCCATAGTTGTTCCAGAA
CAAAATGGTGGAAAATGTGATTATGATCTTAGCAAAATCCAAGAATGCAA
TGTTTCTGTTTGCTCCAAGTCTTGTGATCCTTCTCCATGCTTAAATGGCG
GTATTTGTAGTGAACTACCAAAGTCAAACTTCGCTTGTACATGCCCGCCA
TTTTACGGAGGTGAAACTTGTGATCAATTTGAATTTCCTTGGTGGTTTTA
TAGTGTTATAATTGTTTTAGTTGTTTTGGCTATTGGGATATTTTATAAGT
CACAAATTTCAAATATAGTTACTCCAAATACAATGGATCCTTCATATGCA
GGAGATGGGGATTATGCCTTCAGTCAAGGCCCTGGTCCCCCAGATCCATT
GCAAGCAGCAAATGGACAACCTCAATACTACCAAAATACGTATAATTACA
ACTATGGGTATTATGACAATTCTAATGAAGGATATTTGGTAAATAATGAT
GAAGGAAATTGGATGTACTAG
``` and has amino acid sequence:

```
                                        (SEQ ID NO. 12)
MDSINFRSIYIPSAVRYIILLLLWTIFTKNVYSESSEETLLGRSVLDLNK
KNTCEYYGEQDGMFTDSFHSRICIVPEDGLHGKREYENHQKKTFGTIRPN
```

-continued
NKQLSDNKLYRKDDHLTSSIADFDSNSVRIQRKNVDLEAMFGIGKDNNRM

NLNNEAIQSFYSNNETESQDKNATNDYFLFKBGLLKFQEKKILRYYLYDV

GNKVYSDTIAYPENVISENSAFNYLGNYVDVYEISKVSDPPVISWPNMHI

VFIHSQVKSDGTFKFQVYTSSGEIGFYFEVTDNSYKTGCGSYSRVDKSKF

THSANSLIQVQLVRRKFGFNVFVDGTRRTQLDIIDCIASVPTKVQITSGS

GSQIYPKVEDCQISQWTDWSTCSKTCSTGSKARYRSVIMPSMNGGLPCPK

LLDSSPCNADISCSSCQYSEWTMWGECSATCGSGSTTRTRKLLSAAYFIE

SCIDTFQLKSCHGVSCASDCIVTEWSDWSECSTTCGVGSQISTRSIVVPE

QNGGKCDYDLSKIQECNVSVCSKSCDPSPCLNGGICSELPKSNFACTCPP

FYGGETCDQFEFPWWFYSVIIVLVVLAIGIFYKSQISNIVTPNTMDPSYA

GDGDYAFSQGPAPPDPLQAANGQPQYYQNTYNYNYGYYDNSNEGYLVNND

EGNWMY

7) Protein similar to riken cDNA 5830420c20 gene (Chrom 60194, start position 15004, end position 16041) is encoded by the nucleotide sequence:

(SEQ ID NO. 13)
ATGAAAGAATCAGGCACAATTAATTATCTAATAACATTTACATTCATTAT

TCCTTTCGTACTTTCCCAGTCAACATTATTAAATCTTGGTGCAGGGGTA

TACAGGAAAGGAGGGTTTGCACTGACGAAATGCCATGTAACTTTAGATTG

GTTGCTGATTTAGATATGAAGTCAAAGCCAGGGAGTGGGGAAAAGAATTA

CAAAAGTTTATTTCAAAAAGGGTCAATAATACAAGACAAAAGGGGCAACT

ATCGAGTGTACTGGGGAGAAAGTCTGGAACTTAAAAGCGGATATAATGAA

TATGGGAGAGGGATGGAATTAAGTGAGTTGATTTCATATAATGGAATGAT

GCTTGCGGGCGACGACCGTACAGGAATAATTTTTGAAATAACTGATGATG

GAAAAGGAGTAGCACCAAGATATATATTATCTGAAGGTAATGGAAGAACA

GCTAAGGGAATGAAGATTGAGTGGTTTGCTGTAAGAGATGGAATATTGTG

GGTTGGCAGTTTTGGAAAAGAGTTCGTATCAAACGGCATAATAGAAAAAA

GAGATAAATATGTGGGTAGCCACAATTGATAAAAGAGGATATGTTTCACGA

TTTAATTGGAGTTTTGTTTATGAAAAAATTAGGAATTCACTGGGGCGCA

ATATCCAGGTTATTGCATTCATGAAGCAGTGATTTGGAGTCATTTAATGA

GAAAGTGGATATTTTTACCAAGAAGAGTTAGCTTCGATGAGTATGATGAG

GAGAAAGACGAAAAGAGAGGTTCCAATAAAATGATAATTATGACAGATGA

TTTTGAAATTCTTGAAATTATTGACGTAGGATTGATAATACCTGAAAGAG

GTTTTTCTTCTTTAAAATTTCTTCCTGGGTCGTTTGACCAGATAATAGTT

GCAACAAAAAGCGTTGAAGAATCAATTTCAGACACTCAAAAGTCTTTCTT

AACTATATTCACAATAAATGGAAAAATTTTAATGGAAGATTTAGAAGTGC

CTGGAGACTACAAATACGAGGGGATAGAATTTATATAG and has amino acid sequence:

(SEQ ED NO. 14)
MKESGTINYLITFTFIIPFVLSQSTLLNLGAGGIQERRVCTDEMPCNFRL

VADLDMKSKPGSGEKNYKSLFQKGSIIQDKRGNYRVYWGESLELKSGYNE

YGRGMELSELISYNGMMLAGDDRTGIIFEITDDGKGVAPRYILSEGNGRT

AKGMKIEWFAVRDGILWVGSFGKEFVSNGIIEKRDNMWVATIDKRGYVSR

FNWSFVYEKIRNSLGAQYPGYCIHEAVIWSHLMRKWIFLPRRVSFDEYDE

EKDEKRGSNKMIIMTDDFEILEIIDVGLIIPERGFSSLKFLPGSFDQIIV

ATKSVEESISDTQKSFLTIFTINGKILMEDLEVPGDYKYEGIEFI

8) SPFH domain/Band 7 family protein (Chrom 50147, start position 5008, end position 5850) is encoded by the nucleotide sequence:

(SEQ ID NO. 15)
ATGTCGAGAATTGAAAAAGGTTTTAACATCTTAGCTAACTTGGGGATAAT

GCTGGTTGCAGGTGGAAGCATTTTGGCGTCTAATAGTATGTATAACGTGG

ATGCTGGACACAGAGCAATAAAGTTCTCAAGAATACATGGAGTTCAAAAA

AGGATTATGGAGAAGGAACTGATTTTATGCTACCTTGGATTGAAAGACC

AGTGATATTTGACATCAGAGCGAGACCTCGAGTTGTTGTATCTCTAACGG

GAAGTAAAGATCTTCAAATGGTGAATATTACGTGCAGAGTTTTATCAAGG

CCTGATAAAGATAAGCTGGTGGAAATATATAGAAATATAGGGCTGGATCA

CGATGAGAAGATTCTTCCATCAATAATTAATGAAGTGCTAAAATCAGTAG

TGGCTCAGTATAATGCTTCTCAACTACTAACTATGAGAGAAGACGTGAGC

AAAACAATCCGAGATTTACTGGTAAAAAGAGCCCAAGAGTTTAATATTAT

TCTGGATGATGTCTCTTTAACCCATTTAAGCTTTTCTCAGGATTATGAAA

AGGCTGTAGAGTCCAAGCAAGTTGCTCAACAACAAGCAGAAAGAGCGAAA

TATCTTGTTCTCAAGGCAAACGAAGAGAAAAAAAGTACTATTATTAAGGC

TGAAGGCGAAGCAAAAGCTGCAAAACTAATTGGAGATGCGATAAATGAGA

ATCCTGCCTTTATTGCTGTTAAACAGGTGGAGACTTATAGAGAAATCTCT

AATATTTTAGCAAAATCAACTTCTAAATCGCTTATAAATCTTTCATCATT

TTTGCCAAACCTCCCAAATAGTAATTTACAATCATCTTGTTAG and has amino acid sequence:

(SEQ ID NO. 16)
MSRIEKGFNILANLGIMLVAGGSILASNSMYNVDAGHRAIKFSRIHGVQK

RIYGEGTHFMLPWIERPVIFDIRARPRVVVSLTGSKDLQMVNITCRVLSR

PDKDKLVEIYRNIGLDHDEKILPSIINEVLKSVVAQYNASQLLTMREDVS

KTIRDLLVKRAQEFNIILDDVSLTHLSFSQDYEKAVESKQVAQQQAERAK

YLVLKANEEKKSTIIKAEGEAKAAKLIGDAINENPAFIALKQVETYREIS

NILAKSTSKSLINLSSFLPNLPNSNLQSSC

9) UDP-N-acetyl-D-galactosamine:polypeptide N-acetylgalactosaminyltransferase T4 protein (Chrom 70457, start position 44914, end position 46158) is encoded by the nucleotide sequence:

(SEQ ID NO. 17)
ATGAGGAACGCATTCCCTCTCGGGCTGTCAATATGTTATTTGATGTTGAA

AGTTGCATTGACTACTTTTGTTTTTGGGTCAAAAGAAGAGTTTACAACAC

-continued
TCCCTAGAGAATTAATAAACTCTTGGTTGGAAGAAAATGAATATGCTGGA

TTATATGGAAAATCAGATATTTTTTCAATTGTAATAATACCAGACTGTGA

AGATAATGAATTGATTGATGTTACAATAAATAGTATACTTTTGACTGCAA

ATCGAAATTTACTTCATGAAATAATAATTATTTCAAATGATTGTCAAGAC

TCTGGAAAAGATATTAAAAGTTATTTGGGTGAGAAATTCTTGGATAAGCC

TTTGATTAAAATAATTGAGACTGAATTACAAGAATTGGGAGAATTACAGA

ATCTTGGAGCAAATAATTGAACTGGGGAAATCATTTTATTTGTTCCGTCT

GCAACTCTTTTTCCAAAAAATTGGATGTCACCAATAATGAGGAGTTTAAG

TGATAATTATAAATCAATAATAGTTCCAAGATTTAAAAAATTGAATAAAA

ACAAATGGGCATTTTCGAACAATGATCCTGTATATTCACCAAAAATGATG

TTCACAAAAGAATTTGAATTAACAAATATCCATACATTAGATAATAAAGT

TCCAATGTTCTATTCAAAAATCTTTGCAATAACAAAATCATGGTGGTTAA

ATATATCAAAGCTTTCAGATCCAACAATTAACCTGATATTCAAAACGAGT

ATTAACTTTGATATTTCTCTAAGATCATGGAATTGTGGTGGGCGAGTAGC

TCAGATAGCAGAACTGTCATTTGGTGTAACTAAGGTAAAAATCTCACAAC

CTTCGTTAGAAATAAGACAAGTTCTATTGGAATCTTGGATAGATGAGCCA

ACCAAGCAGATGATTATGAATAATAGTGAGAAGCTGGCTAACTATATGAA

ACTATCATCAGGATTATTTGAGGTATTGATAAATAAACGTAAGGAACTCA

TTAAAGAGTATGAATGTGACCAAAAGTCAATATTTACTTCAAAATTTTAT

AATGAGTTGAGCGAATTTGGACTAATAGAATATCCAAAAAGTCAAATAGT

TTTTAGTGGTAATGGCAAATGCTTCACATTAATTGGGAACGAGAAAAAAA

GTGGAGAAAAGAATTTCGAGTTAAAGTTATCAGAATGTAAACCAATGAA

AATGCACAAATATTCTACATTGACAATGAGAGTAAGTTGATCTAG and has amino acid sequence:

(SEQ ID NO. 18)
MRNAFPLGLSICYLMLKVALTTFVFGSKEEFTTLPRELINSWLEENEYAG

LYGKSDIFSIVIIPDCEDNELIDVTINSILLTANRNLLHEIIISNDCQD

SGKDIKSYLGEKFLDKPLIKIIETELQELGELQNLGANNSTGEIIILFVP

SATLFPKNWMSPIMRSLSDNYKSIIVPRFKKLNKNKWAFSNNDPVYSPKM

MFTKEFELTNIHTLDNKVPMFYSKIFAITKSWWLNISKLSDPTINLIFKT

SINFDISLRSWNCGGRVAQIAELSFGVTKVKISQPSLEIRQVLLESWIDE

PTKQMIMNNSEKLANYMKLSSGLFEVLINKRKELIKEYECDQKSIFTSKF

YNELSEFGLIEYPKSQIVFSGNGKCFTLIGNEKKSGEKNFELKLSECKPN

ENAQIFYIDNESKLI

10) ABC transporter ATP-binding protein (Chro.70309, start position 5325, end position 7046) is encoded by the nucleotide sequence:

(SEQ ID NO. 19)
ATGCTTATTATAAACGGAGCAATTAATTGTGCTAGAACTGATATGTCGAT

TCGAATTCAAATTGATTTAAGGATGTGGCTAACTAATTTGATTTTGAAAC

AATATTATTCTGATTTAACTTACTATCAGTTCTCAATAAATAAAACGATT

GATAATCCTGACCAAAGAATTGGAGAGGACATTTCACTGTTTTCATCACA

TTTATTATTGTTAATATGTCGTTGTATAGACAACTTATTTGACTTTTTTG

TTTATTCAATCTTGCTATACAATGTTAATTTCAAATTGTTTATTTCAGCA

ATTATTTATTCTTGTTTTGGCACATTTTTAACTGCTAAATTAGGCATGAA

TATAATATTATTAAAAGTTCAAGAAAAAAAGCTTGAAAGTGATTTTAGAT

ATTCAATTATGAGAGTTGGTGAAAATGCAGAAAATGTTGCAATGTATGGA

GGAGCTCAGTGCGAGATGGAAAGACATGAACAAATTTTAAATTCATTGCT

TCTCAACTTAACTACGAAAAGATCATTTGAATCTAAAATGGGACTCTTTG

GAAGTATTTTTAGAAACCTAATACGTGTTCTGCCTATTGCGGTTATTTCA

GGAGACTACTTTTCAGGAAATATCCAACTTGGAAGAATTAATCAGTGTAG

CCTTGCATTTAACAGTATAGTTGAAGATATTTCAATTTTGGTCAATACTT

TTAGAGAAATAAGTAATCTACTTTCTTCAATAGATAGAGTAGGACATTTT

ATTGCATTGATGGCAGATAACTATATTGAATCTCAATCTATAAATATTGG

AGAGAAATTGATTAGTAGTTTTGAGAGTGATTCTAAAACTAGCAAAAAAA

TTGATTTCTTACATCTTGAAAGCGAGTTTTCAAGACAAATGAAGGAAAAA

TCTTTAGAATTTAAACTTAATTTCTCGACAGGAATTGCTTCTAAGTCATT

AAAAAATTGTGTTAAATTAGAATTTACAAACACTCAGGGGAAATCTTCGG

TTAATATACGTGGAAAAATTAGATCAGTAATATGGCCAGAACCAAAAATT

AAGTTTGAAAGTGTATCGATTAATACTCCGGAAGAATATCCCAGGAAACT

TCTTTTTAATATAAACTTTATGATTGAACAAAGCGATAAAGTCTTAATAA

CAGGGGACTCCGGTGTTGGGAAATCATCACTCTTAAAGGTAATTTGTGGG

ATTTGGAATAATGGGTCAGGAAATATTTATAGGCCACCTTCTAGTGAATT

ATTATTTATACCGCAAAAACCCTACTGTACCCAAGCAACGCTAAGGGAAC

AACTGTTTTATCCGCAAATACCCTCAATTAAAACTAATGGTTATGAATAT

AAAAATAAGGAAGAACTAGATTCATATCTATTGAAAATTCTTGAGGAAGT

TGGGCTGAAATATCTATGTGATCGACTTTCTGAAAGTGAAACAGTTAATT

GCTTAGACACCATTAAAGACTGGTCAACAATACTTTCGCTTGGAGAACAG

CAAAGACTTGCATTTGCAAGAATATTTATTTTCAAACCATCTATTTGTTT

CCTTGATGAAGCTACAAGTGCGTTAGACATGGAGACTGAAACAAAATTAT

ATTCAATGCTAAATAAAAAAAACTTTACATACGTTAGTGTAGGTCACAGG

CCCTCAATATCAATATTTCACAACAAAAAAGTCCTTATAAAAAATGGTAA

TATAATTTTTGAATGTATATGA and has amino acid sequence:

(SEQ ID NO. 20)
MLIINGAINCARTDMSIRIQIDLRMWLTNLILKQYYSDLTYYQFSINKTI

DNPDQRIGEDISLFSSHLLLLICRCIDNLFDFFVYSILLYNVNFKLFISA

IIYSCFGTFLTAKLGMNIILLKVQEKKLESDFRYSIMRVGENAENVAMYG

GAQCEMRRHEQILNSLLLNLTTKRSFESKMGLFGSIFRNLIRVLPIAVIS

GDYFSGNIQLGRINQCSLAFNSIVEDISILVNTFREISNLLSSIDRVGLF

IALMADNYIESQSINIGEKLISSFESDSKTSKKIDFLHLESEFSRQMKEK

-continued

SLEFKLNFSTGIASKSLKNCVKLEFTNTQGKSSVNIRGKIRSVIWPEPKI

KFESVSINTPEEYPRKLLFNINFMIEQSDKVLITGDSGVGKSSLLKVICG

IWNNGSGNIYRPPSSELLFIPQKPYCTQATLREQLFYPQIFSIKTNGYEY

KNKEELDSYLLKILEEVGLKYLCDRLSESETVNCLDTIKDWSTILSLGEQ

QRLAFARIFIFKPSICFLDEATSALDMETETKLYSMLNKKNFTYVSVGHR

PSISIFHNKKVLIKNGNIIFECI

11) Sporozoite cysteine-rich protein (Chro.60102, start position 11337, end position 12380) is encoded by the nucleotide sequence:

(SEQ ID NO. 21)
ATGTTAGAATTTAGACAATATGATTTAAAGTTTATGAAAATGAAAGAAT

TTTGTATTTTATATTAATACATATTCTTATATTTAATATTTTAGAAATAA

ATTCTTTACCACCAAGTTTTAGTTGGACAAAAGCATGGAAAGATATTACC

AGTGAAGGGTTAGTATATACATTTAGTTCAAATAAGCTACCTTGGTATTC

TGGAGTATCTTTTAGGATTGTGGGTAAATTTAACGCAGAAAATGATAAAG

AAACTTTGGTAACAATTCAGAATGGTGATTTATACCACTGTAAGTTGATT

ATAAATTTTGCAGCACAAACAGTAGATGTGGAATCTACAGGATATACTGC

AGAAGAGAGATGGGCTAGATCTTATGCTTACTTTCCATTTCCATATAAGC

CAAAATTGATGGATCTTGACTTGGTAGTTGAGAAATTAAGATGGCCAGGA

GGGTTTTACTTTTATATTTCAGGAAGTGGACCATATTATCCTTGTCATAG

CATAGTGTATTCAAATGTGAATAAATTAACTTTTGGTAATGGACAAAATA

ACTTTAGTAAATATAAAATTACAAGAAATGTTCCTTTGGCAGATCCTTAT

AGAAGGACTTATTTCTGGGACGAATTTCAACAAAGATACTATTTTGATGA

TAAAAATTTGTATTATGTAAATAGCACCGGAATTGATGAGAAAATCTGGA

GTACCAAATGGTGATAGAATTCCAAAACATTATAAATCTTGGCCAGAAGA

ACTAGAAATACATGTACATTCAGCAAGTATGTACCCAGTTAATGATAAAA

GATACGGATGGGGAGGTACGGTAGCAGTATTTACAAGCGATCAGAGTCAG

TTTTATTATAGAATGAATGGATTTTTTGCAACTTTGTCAAGTAATTCATA

TTGTTTAAGTTCGAGTGTATTATTAAGTGGGACAAGTTATACAGTTAGTG

GAGATTATCCTTTTGATTTTGATAATCCAGGTCAACCTTTCAATGTAAGT

TTACTTATGATTATTAAGATAATAAGCCTATTTATTATGAGGTAG and has amino acid sequence:

(SEQ ID NO. 22)
MLEFRQYDLKFMKMKRILYFILIHILIFNILEINSLPPSFSWTKAWKDIT

SEGLVYTFSSNKLPWYSGVSFRIVGKFNAENDKETLVTIQNGDLYHCKLI

INFAAQTVDVESTGYTAEERWARSYAYFPFPYKPKLMDLDLVVEKLRWPG

GFYFYISGSGPYYPCHSIVYSNVNKLTFGNGQNNFSKYKITRNVPLADPY

RRTYFWDEFQQRYYFDDKNLYYVNSTGIDEKSGVPNGDRIPKHYKSWPEE

LEIHVHSASMYPVNDKRYGWGGTVAVFTSDQSQFYYRMNGFFATLSSNSY

CLSSSVLLSGTSYTVSGDYPFDFDNPGQPFNVSLLMIIKIISLFIMR 12) 19K sporozoite antigen "profilin" (Chro.30189 start position 2297, end position 2785) is encoded by the nucleotide sequence:

(SEQ ID NO. 23)
ATGTCTGAATGGGATGATATGGTCAAAGAATGGTTAATTGACACCGGTAG

TGTATGTGCTGGTGGTCTTTGTTCAATAGATGGTGCATTCTATGCTGCTT

CTGCTGATCAAGGTGATGCCTGGAAGACTCTTGTTAGAGAAGATCATGAA

GAAAATGTTATTCAATCCGACGGAGTTTCAGAGGCTGCTGAATTAATTAA

TGATCAAACTACACTATGCCAAGCTATCTCTGAGGGTAAGGCACCAAACG

GCGTTTGGGTCGGAGGAAACAAATATAAGATTATCCGCGTAGAGAAGGAC

TTCCAACAAAACGATGCTATTGTTAATGTTACATTCTGTAACAAACCTCA

AGGTGGATGTTTTTTAGTTGATACTCAAAACGGTACTGTTGTCGTTGCGG

TTTACGACGAATCCAAAGATCAATCATCAGGTAATTGCAAGAAGGTTGCT

TTGCAACTGGCCGAGTACCTCGTATCTCAGGGATACTAA and has amino acid sequence:

(SEQ ID NO. 24)
MSEWDDMVKEWLIDTGSVCAGGLCSIDGAFYAASADQGDAWKTLVREDHE

ENVIQSDGVSEAAELINDQTTLCQAISEGKAPNGVWVGGNKYKIIRVEKD

FQQNDAIVNVTFCNKPQGGCFLVDTQNGTVVVAVYDESKDQSSGNCKKVA

LQLAEYLVSQGY

Example 3

Immunotherapy

*C. hominis* proteins have been overexpressed in *E. coli* and isolated, and are tested in model systems to examine their abilities to induce a protective immune response. Animal models of *Cryptosporidium* infection have demonstrated the role of both cell and humoral immune responses (1, 2). Thus, mice with targeted disruptions of genes encoding immunological important molecules have established the role of these proteins in the immune response against *Cryptosporidium* (1-7). Other studies of the immune response against *Cryptosporidium* use neonatal mice and mice lacking functional T or B cell responses (1, 8, 9). These studies have demonstrated how an immune response is induced in mice that are not immuno-competent. Adult mice are resistant to the infection with *Cryptosporidium* but the injection of an antibody against Interferon Gamma (IFN γ) prior to infection render them susceptible to *Cryptosporidium* (10, 13). IFN γ plays an important role in the induction of an immune response against many microorganisms, and many studies have shown that it is one of the key components of the immune response against *Cryptosporidium* infections (11-17). Thus the temporary neutralization of IFN γ by the administration of the antibody in adult mice is an excellent tool to study and characterize the immune response in the context of an immunocompetent animal (10).

The IFN knockdown mouse model follows a pattern of infection very similar to that seen in severe clinical infections (10). During the infection the animals lost weight and then regained it during recovery. This is also similar to what is observed in metabolically stressed children during and after diarrheal diseases. The predominant site of infection was the small intestine as it has been observed in animal and human severe infections. No parasites can be detected by day 30, thus the level of infection achieved is enough to generate an immune response, which also it is demonstrated by the detection of cellular responses against *Cryptosporidium* antigen extracts and proteins with lymphocytes obtained from the treated animals. Thus this model offers the possibility to study the potential role of *Cryptosporidium* as the animal can mount a parasite specific immune response (10).

We use this model (and alternative models such as a malnourished mouse model, unpublished) to study the potential role of *Cryptosporidium* recombinant proteins and plasmid DNA containing *Cryptosporidium* genes to induce an immune response. Our protocol to carry out this study is outlined in brief below. Subject mice are divided in groups: Group I mice are immunized with a pool of recombinant antigens (or plasmids in the case of DNA vaccine) in adjuvant (Freund's or other as appropriate); Group II (control animals) are immunized with Freund's adjuvant alone (or plasmid with no insert in the case of a DNA vaccine). The immunological responses in each group are followed and the response to challenge is measured. A sample immunization schedule is outlined below:

1) Day 0: Immunization with a pool of recombinant antigens (2-3 μg each), DNA (20-100 μg) or controls. Immunization is performed intraperitoneally or intranasally.
2) Day 14: Boost Immunization with the same antigens (protein, DNA, control). Boost is administered intranasally.
3) Day 28: Anti-IFN-γ Ab inoculation, intraperitoneally, 2 h prior to *Cryptosporidium* infection.
4) Day 28 (2 hr after inoculation of anti-IFN-γ Ab): Infection with *Cryptosporidium.*

The immune response and protection to infection is monitored. A sample protocol is outlined below:

1) Serum samples are collected at day 0, 7, 14 and 28 to monitor the immune response. Antibody levels against fusion proteins and *Cryptosporidium* extract are measured by immunoblotting and indirect immunofluorescence.
2) Fecal IgA responses are measured before and after vaccination and infection.
3) Fecal shedding of *Cryptosporidium* is monitored by fluorescent microscopy and real time PCR three times per week after infection
4) Cytokine and lymphoproliferation responses are examined by isolation of mesenteric lymphocyte node and spleen cells to detect cytokine responses and lymphoproliferation against antigens (those that can be purified) and against a *Cryptosporidium* preparation.

These results indicate proteins which induce an antibody (mucosal or humoral) or cellular immune response. More important, these results indicate which immune response is protective and reduces infection (and shedding) by the exposed animal.

REFERENCES FOR EXAMPLE 3

1. Riggs M W. Recent advances in cryptosporidiosis: the immune response. Microbes Infect. 2002. (10): 1067-80.
2. Lean I S, McDonald V, Pollok R C. The role of cytolines in the pathogenesis of *Cryptosporidium* infection. Curr Opin Infect Dis. 2002. 15(3): 229-34.
3. Ehigiator H N, Romagnoli P, Borgelt K, Fernandez M, McNair N, Secor W E, Mead J R. Mucosal cytokine and antigen-specific responses to *Cryptosporidium parvum* in IL-12p40 KO mice. Parasite Immunol. 2005. 27(1-2): 17-28.
4. Chen W, Harp J A, Harmsen A G. *Cryptosporidium parvum* infection in gene-targeted B cell-deficient mice. J. Parasitol. 2003. 89(2): 391-3.
5. Davami M H, Bancroft G J, McDonald V. *Cryptosporidium* infection in major histocompatibility complex congeneic strains of mice: variation in susceptibility and the role of T-cell cytokine responses. Parasitol Res. 1997. 83(3): 257-63.
6: Lacroix S, Mancassola R, Naciri M, Laurent F. *Cryptosporidium parvum*-specific mucosal immune response in C57BL/6 neonatal and gamma interferon-deficient mice: role of tumor necrosis factor alpha in protection. Infect Immun. 2001. 69(3): 1635-42.
7. McDonald S A, O'Grady J E, Bajaj-Elliott M, Notley C A, Alexander J, Brombacher F, McDonald V. Protection against the early acute phase of *Cryptosporidium parvum* infection conferred by interleukin-4-induced expression of T helper 1 cytokines. J Infect Dis. 2004. 190(5): 1019-25.
8. McDonald V, Deer R, Uni S, Iseki M, Bancroft G J. Immune responses to *Cryptosporidium muris* and *Cryptosporidium parvum* in adult immunocompetent or immunocompromised (nude and SCID) mice. Infect Immun. 1992. 60(8): 3325-31.
9. Kuhls T L, Greenfield R A, Mosier D A, Crawford D L, Joyce W A. Cryptosporidiosis in adult and neonatal mice with severe combined immunodeficiency. J. Comp Pathol. 1992. 106(4): 399-410.
10. Theodos C M, Sullivan K L, Griffiths J K, Tzipori S. Profiles of healing and nonhealing *Cryptosporidium parvum* infection in C57BL/6 mice with functional B and T lymphocytes: the extent of gamma interferon modulation determines the outcome of infection. Infect Immun. 1997 65(11): 4761-9.
11. You X, Mead J R. Characterization of experimental *Cryptosporidium parvum* infection in IFN-gamma knockout mice. Parasitology. 1998. 117: 525-31.
12. Mead J R, You X. Susceptibility differences to *Cryptosporidium parvum* infection in two strains of gamma interferon knockout mice. J. Parasitol. 1998. 84(5): 1045-8
13. Griffiths J K, Theodos C, Paris M, Tzipori S. The gamma interferon gene knockout mouse: a highly sensitive model for evaluation of therapeutic agents against *Cryptosporidium parvum*. J Clin Microbiol. 1998. 36(9): 2503-8.
14. Pollok R C, Farthing M J, Bajaj-Elliott M, Sanderson I R, McDonald V. Interferon gamma induces enterocyte resistance against infection by the intracellular pathogen *Cryptosporidium parvum*. Gastroenterology. 2001. 20: 99-107.
15. Aguirre S A, Perryman L E, Davis W C, McGuire T C. IL-4 protects adult C57BL/6 mice from prolonged *Cryptosporidium parvum* infection: analysis of CD4+alpha beta+IFN− gamma+ and CD4+alpha beta+IL-4+lymphocytes in gut-associated lymphoid tissue during resolution of infection. J. Immunol. 1998. 161: 1891-900.
16: Lehmann J, Enssle K H, Lehmann I, Emmendorfer A, Lohmann-Matthes M L. The capacity to produce IFN-gamma rather than the presence of interleukin-4 determines the resistance and the degree of susceptibility to *Leishmania donovani* infection in mice. J Interferon Cytokine Res. 2000. 20: 63-77.
17. Lacroix S, Mancassola R, Naciri M, Laurent F. *Cryptosporidium parvum*-specific mucosal immune response in C57BL/6 neonatal and gamma interferon-deficient mice: role of tumor necrosis factor alpha in protection. Infect Immun. 2001. 69: 1635-42.

Example 4

Development of Chemotherapeutic Agents

The approach to the development of chemotherapeutic intervention strategies parallels the selection of candidate vaccinogens using genome sequence data and informatics approaches. The rationale is that weak links in the parasite's biology can be identified by examining its genome. For example, several hundred likely essential transporter proteins that are responsible for importing essential nutrients into the parasite have been identified (see Table 3). Without these transporters, the parasite is unable to obtain required building blocks and therefore is unable to survive. Inhibition of one or more transporters (for example, by small molecule inhibitors or by antibodies) is a useful strategy for prevention or treatment of the *C. hominis* related disease.

The process for development of these agents includes the following steps:

1) Informatic pathway annotation and analysis to identify the processes known to be active in the parasite. This work has been completed, although updates are included with technology advances.
2) Network and topological analysis are applied to identify nodes that are considered 'critical elements' or 'essential steps'. This analysis involves a series of mathematical and computational steps to identify those proteins that, when inhibited, are most likely to result in death or growth inhibition of the parasite. Examples of such 'critical elements' include transporters for essential nutrients (ions, amino acids, nucleotides, sugars, etc.) for which no substitute is available, essential steps in energy metabolism (e.g., glycolysis, regeneration of NADP, etc.), intermediary metabolism (e.g., carbohydrate anabolism and catabolism), biosynthesis (nucleotide interconversion, amino acid interconversion, synthesis of amylopectin, fatty acid biosynthesis), and other essential pathways.
3) Genes that encode proteins that are deemed likely to be 'critical elements' according to step 2, are cloned and expressed in bacterial systems as outlined above. The gene products (proteins) are then tested for activity and examined for inhibition by libraries of potential inhibitory compounds. This is performed in collaboration with pharmaceutical companies that maintain batteries of such compounds.
4) In parallel with #3, the proteins are crystallized and subjected to X-Ray crystallography to identify their 3D structures.
5) The 3D structures are used in 'rational drug design' to identify categories of potentially inhibitory compounds.

For example, we have identified the zinc transporter (see above) as a focus of these investigations. *Cryptosporidium*, like all living organisms, requires divalent cations like zinc. This compound must be actively imported into the cell. In the absence of zinc, or if the organism is unable to import it from its surroundings, *Cryptosporidium* will die. Thus, we have cloned and expressed the *Cryptosporidium* zinc transporter and will now search for compounds that inhibit its activity. In parallel, the structure of the transporter will be determined to further guide selection of potential inhibitory compounds.

Example 5

Development of DNA Vaccine

Plasmid DNA was also isolated using the EndoFree plasmid Giga Kit (Qiagen) and is used as an antigen to be injected in mice to test their protective role against *Cryptosporidium*. Animal models of *Cryptosporidium* infection have demonstrated the role of both cell and humoral immune responses (1, 2). Thus, mice with targeted disruptions of genes encoding immunological important molecules have established the role of these proteins in the immune response against *Cryptosporidium* (1-7). Other studies of the immune response against *Cryptosporidium* use neonatal mice and mice lacking functional T or B cell responses (1, 8, 9). These studies have demonstrated how an immune response is induced in mice that are not immuno-competent. Adult mice are resistant to the infection with *Cryptosporidium* but the injection of an antibody against Interferon Gamma (IFN γ) prior to infection render them susceptible to *Cryptosporidium* (10, 13). IFN γ plays an important role in the induction of an immune response against many microorganisms, and many studies have shown that it is one of the key components of the immune response against *Cryptosporidium* infections (11-17). Thus the temporary neutralization of IFN γ by the administration of the antibody in adult mice is an excellent tool to study and characterize the immune response in the context of an immunocompetent animal (c.f., 10).

The IFN knockdown mouse model follows a pattern of infection very similar to that seen in severe clinical infections (10). During the infection the animals lost weight and then regained it during recovery. This is also similar to what is observed in metabolically stressed children during and after diarrheal diseases. The predominant site of infection was the small intestine as it has been observed in animal and human severe infections. No parasites can be detected by day 30, thus the level of infection achieved is enough to generate an immune response, which also it is demonstrated by the detection of cellular responses against *Cryptosporidium* antigen extracts and proteins with lymphocytes obtained from the treated animals. Thus this model offers the possibility to study the potential role of *Cryptosporidium* as the animal can mount a parasite specific immune response (10).

We use this model (and alternative models such as a malnourished mouse model, unpublished) to study the potential role of *Cryptosporidium* recombinant proteins and plasmid DNA containing *Cryptosporidium* genes to induce an immune response. Our protocol to carry out this study is outlined in brief below. Subject mice are divided in groups: Group I mice are immunized with a pool of recombinant antigens (or plasmids in the case of DNA vaccine) in adjuvant (Freund's or other as appropriate); Group II (control animals) are immunized with Freund's adjuvant alone (or plasmid with no insert in the case of a DNA vaccine). The immunological responses in each group are followed and the response to challenge is measured. A sample immunization schedule is outlined below:

1) Day 0: Immunization with a pool of recombinant antigens (2-3 μg each), DNA (20-100 μg) or controls. Immunization is performed intraperitoneally or intranasally.
2) Day 14: Boost Immunization with the same antigens (protein, DNA, control). Boost is administered intranasally.
3) Day 28: Anti-IFN-γ Ab inoculation, intraperitoneally, 2 h prior to *Cryptosporidium* infection.
4) Day 28 (2 hr after inoculation of anti-IFN-γ Ab): Infection with *Cryptosporidium.*

The immune response and protection to infection is subsequently monitored. A sample protocol is outlined below:
5) Serum samples are collected at day 0, 7, 14 and 28 to monitor the immune response. Antibody levels against fusion proteins and *Cryptosporidium* extract are measured by immunoblotting and indirect immunofluorescence.
6) Fecal IgA responses are measured before and after vaccination and infection.
7) Fecal shedding of *Cryptosporidium* is monitored by fluorescent microscopy and real time PCR three times per week after infection
8) Cytokine and lymphoproliferation responses are examined by isolation of mesenteric lymphocyte node and spleen cells to detect cytokine responses and lymphoproliferation against antigens (those that can be purified) and against a *Cryptosporidium* preparation.

These results indicate proteins which induce an antibody (mucosal or humoral) or cellular immune response. More important, these results indicate which immune response is protective and reduces infection (and shedding) by the exposed animal.

REFERENCES FOR EXAMPLE 5

1. Aguilar-Be I, da Silva Zardo R, Paraguai de Souza E, Borja-Cabrera G P, Rosado-Vallado M, Mut-Martin M, Garcia-Miss Mdel R, Palatnik de Sousa C B, Dumonteil E. Cross-protective efficacy of a prophylactic *Leishmania donovani* DNA vaccine against visceral and cutaneous murine leishmaniasis. Infect Immun. 2005 February; 73(2):812-9.
2. Aguiar J C, LaBaer J, Blair P L, Shamailova V Y, Koundinya M, Russell J A, Huang F, Mar W, Anthony R M, Witney A, Caruana S R, Brizuela L, Sacci J B Jr, Hoffman S L, Carucci D J. High-throughput generation of *P. falciparum* functional molecules by recombinational cloning. Genome Res. 2004 October; 14(10B):2076-82.
3. Wu S Q, Wang M, Liu Q, Zhu Y J, Suo X, Jiang J S. Construction of DNA vaccines and their induced protective immunity against experimental *Eimeria tenella* infection. Parasitol Res. 2004 November; 94(5):332-6.
4. Tborra S, Soto M, Carrion J, Alonso C, Requena J M. Vaccination with a plasmid DNA cocktail encoding the nucleosomal histones of *Leishmania* confers protection against murine cutaneous leishmaniosis. Vaccine. 2004 Sep. 28; 22(29-30):3865-76.
5. Sagodira S, Iochmann S, Mevelec M N, Dimier-Poisson I, Bout D. Nasal immunization of mice with *Cryptosporidium parvum* DNA induces systemic and intestinal immune responses. Parasite Immunol. 1999 October; 21(10):507-16.
6. Sagodira S, Buzoni-Gatel D, Iochmann S, Naciri M, Bout D. Protection of kids against *Cryptosporidium parvum* infection after immunization of dams with CP15-DNA. Vaccine. 1999 May 14; 17(19):2346-55.
7. Jenkins M, Kerr D, Fayer R, Wall R. Serum and colostrum antibody responses induced by jet-injection of sheep with DNA encoding a *Cryptosporidium parvum* antigen. Vaccine. 1995 December; 13(17):1658-64.
8. Huygen K. Plasmid DNA vaccination. Microbes Infect. 2005 May; 7(5-6):932-8.
9. Barouch D H, Letvin N L, Seder R A. The role of cytokine DNAs as vaccine adjuvants for optimizing cellular immune responses. Immunol Rev. 2004 December; 202: 266-74.
10. Sukumaran B, Madhubala R. Leishmaniasis: current status of vaccine development. Curr Mol. Med. 2004 September; 4(6):667-79.
11. Barry M A, Howell D P, Andersson H A, Chen J L, Singh R A. Expression library immunization to discover and improve vaccine antigens. Immunol Rev. 2004 June; 199: 68-83.
12. Leifert J A, Rodriguez-Carreno M P, Rodriguez F, Whitton J L. Targeting plasmid-encoded proteins to the antigen presentation pathways. Immunol Rev. 2004 June; 199:40-53.
13. Howarth M, Elliott T. The processing of antigens delivered as DNA vaccines. Immunol Rev. 2004 June; 199:27-39.
14. Xu F, Ulmer J B. Attenuated *salmonella* and *Shigella* as carriers for DNA vaccines. J Drug Target. 2003; 11(8-10): 481-8.
15. Aguirre S A, Perryman L E, Davis W C, McGuire T C. IL-4 protects adult C57BL/6 mice from prolonged *Cryptosporidium parvum* infection: analysis of CD4+alpha beta+IFN-gamma+ and CD4+alpha beta+IL-4+lymphocytes in gut-associated lymphoid tissue during resolution of infection. J Immunol. 1998. 161: 1891-900.
16. Lehmann J, Enssle K H, Lehmann I, Emmendorfer A, Lohmann-Matthes M L. The capacity to produce IFN-gamma rather than the presence of interleukin-4 determines the resistance and the degree of susceptibility to *Leishmania donovani* infection in mice. J Interferon Cytokine Res. 2000. 20(1): 63-77.

Example 6

Detection and Diagnostics

Detection and diagnosis of *C. hominis* infection are very difficult and are typically based on microscopic examination (of water supplied or stool, etc.). A small number of previously characterized genes are now used for detection and diagnosis. These genes differ from their homologs in closely related parasites and therefore form the basis of a genetic signature. However, current protocols are limited in scope and could result in errors in identification. We have compared all the genes of *C. hominis* to many other related parasites, have identified important signature nucleotide sequences, which serve as the basis for the development of improved diagnostic tools. The signature nucleotide sequences are unique to *C. hominis* (see Table 9). Detection of the unique, signature sequences using nucleotide probes specific for them, provides a highly reliable method of detecting the presence of *C. hominis* in abiological sample, and thus for the diagnosis of a *C. hominis* infection.

As important as detection and diagnosis, it is important to quantify *Cryptosporidium* in an infected sample to assess the seriousness of the disease or contamination. Thus, *Cryptosporidium* are common in the environment and small quantities of the organism in water samples or in fecal samples are not uncommon. Using the signature nucleotide sequences described in Table 9, it is possible to both specifically identify and to accurately quantify levels of *Cryptosporidium* in essentially any biological or environmental sample. An example of such use is described below.

Real Time PCR(RT-PCR) Analysis of Detection, Quantification and Diagnosis

The example below used TaqMan® assay system technology (Applied Biosystems, Foster City, Calif.), but any fluorescent real time PCR technology (of many that are commercially available) can be similarly applied (1, 2, 3). In brief, oligonucleotide primers and probes specific for sequences of *Cryptosporidium* small subunit ribosomal RNA gene and the pyruvate kinase genes were designed (4, 5) using Primer Express® version 2.0 software. These sequences were selected among the many available in Table 9 because of historical precedent. However, nearly all of the sequences described in Table 9 could be used by one trained in the art as specific targets in these analyses. For each target, two primers (forward and reverse) flanking one internal probe are synthesized. The primers are synthesized without modified bases or labels. The probes are synthesized with 5' end linked FAM (6-carboxyfluoresceine) and 3' end fluorescent TAMRA (6-carboxytetramethylrhodamine) dyes. These fluorescent dyes are commonly used for TaqMan® assay system technology, but many other labeling systems are equally applicable. Primers and Probes for the Small Subunit rRNA Gene and the Pyruvate Kinase Gene.

```
Small Subunit rRNA
Name (forward): 18S#2-295F
Sequence:
CAGCTTTAGACGGTAGGGTATTGG     (SEQ ID NO: 4060)

Name (reverse): 18S#2-368R
Sequence:
TCTCCGGAATCGAACCCTAAT        (SEQ ID NO: 4061)

Name (probe): 18S#2-324T
Sequence:
CCCGTTACCCGTCATTGCCACG       (SEQ ID NO: 4062)

Pyruvate kinase
Name (forward): pyruvate kinase-1016F
Sequence:
GGCCAACAAGGGCAGAAA           (SEQ ID NO: 4063)

Name (reverse): pyruvate kinase-1091R
Sequence:
TCTCCAGATAGCATAACACAATCTGA   (SEQ ID NO: 4064)

Name (probe): pyruvate kinase-1040T
Sequence:
ATGTTGCAAACGCTGTTTTAGATG     (SEQ ID NO: 4065)
```

Synthesis of all primers and probes were performed at the VCU Nucleic Acids Research Facilities.

We tested the effectiveness of the primers above to detect parasite sequences in total RNA of the human cell line HCT-8 infected with *Cryptosporidium*. However, with insignificant modifications, this procedure is equally effective for detection and quantification of *Cryptosporidium* in other samples (e.g., water samples, fecal samples, sputum or bronchalveolar lavage, serum, etc.). In addition, this procedure is equally effective if the target is DNA instead of RNA. Thus, this example is provided as a general validation of this approach to *Cryptosporidium* detection and quantification.

Live (LV) and heat inactivated (HI) parasites were used to infect monolayers of cultured HCT-8 human cell line. RNA was isolated from these infected cell lines using standard procedures for purification of total RNA. Assays to quantify the *Cryptosporidium* RNA in these cells using the primers described above were performed in VCU's Nucleic Acids Research Facilities in an ABI Prism® 7900 Sequence Detection System (SDS) (Applied Biosystems, Foster City, Calif.) using the TaqMan® One Step PCR Master Mix Reagents Kit (P/N: 4309169). Again, any other real time PCR system would be equally applicable to this technological approach. All samples were processed in triplicate following standard procedures established in the Nucleic Acids Research Facilities.

Figure 2A:
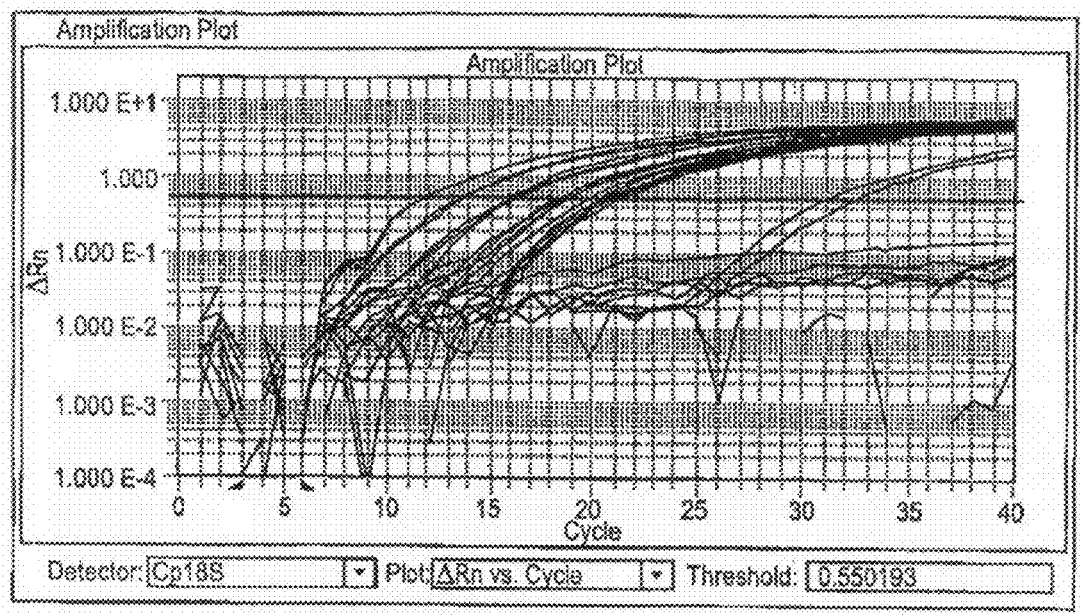
Figure 2B:
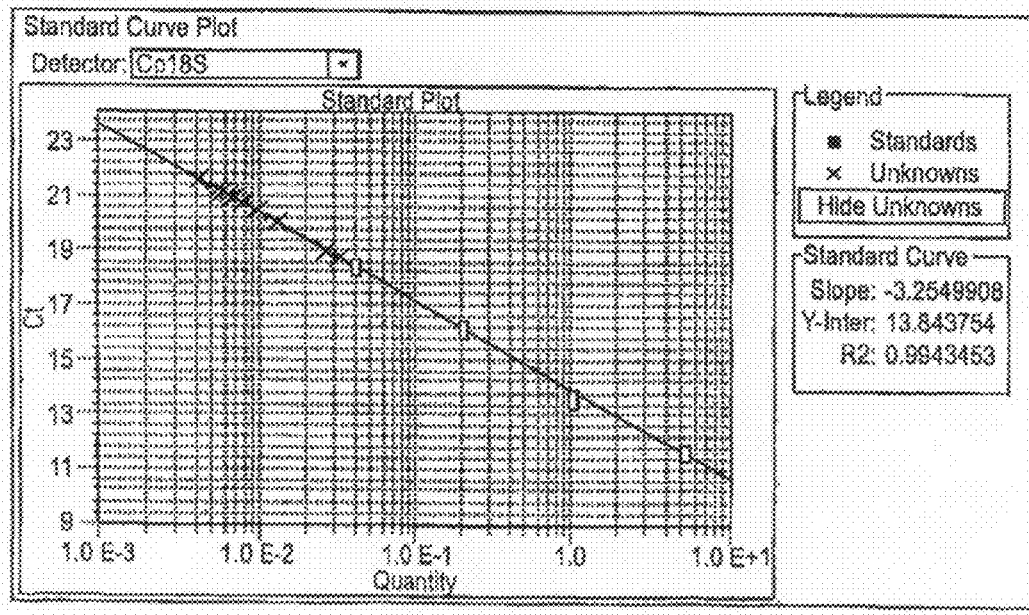

The FIG. 2 shows typical amplification curve plots (A) generated by these samples and a standard curve plot of known amounts of *Cryptosporidium* rRNA, for measuring the absolute quantities of *Cryptosporidium* small sufigurebunit rRNA in the samples (B). The table below shows the numerical results of the parasite RNA quantification. These results showed that the *Cryptosporidium* RNA is present only in the samples in which infection was mediated with live parasites. As expected, heat inactivated parasites do not infect, and no parasite RNA is observed. Moreover, the results indicate that the amount of *Cryptosporidium* RNA present varies from approximately 5-30 picograms, permitting a direct calculation of the number of parasites present in the sample.

*C. hominis* is the primary agent of human cryptosporidiosis. *C. parvum* is a common cause of disease in animals, and an occasional problem in humans. It is important to differentiate between these two (and other) strains of *Cryptosporidium*. Our technology enables the ready discrimination of these isolates. Thus, we have demonstrated that we can use the sequences we have described in Table 9 for differentiating *C. parvum* from *C. hominis*. In brief, the same technology outlined above; e.g., RT PCR using primer and probe sets specific for *C. hominis* or *C. parvum* are used to amplify RNA (or DNA) purified from a sample (water, fecal material, other sample). In these amplifications, we can not only detect and discriminate different *Cryptosporidium* strains (e.g., *C. hominis* from *C. parvum*), but each can be concurrently quantified.

REFERENCES FOR EXAMPLE 6

1. Wang, A. M., Doyle, M. V., and D. F. Mark. (1989) Quantitation of mRNA by the polymerase chain reaction. Proc Natl Acad Sci USA. 1989 December; 86(24): 9717-9721.
2. Kawasaki, E. S., and A. M. Wang. (1989) Detection of gene expression. In: Erlich, H. A., ed., PCR Technology: Principles and Applications of DNA Amplification. Stockton Press, Inc., New York, N.Y., pp. 89-97.
3. Dieter Klein (2002) Quantification using real-time PCR technology: applications and limitations. Trends in Molecular Medicine, 8(6):257-260.
4. Xu P, Widmer G, Wang Y, Ozaki L S, Alves J M, Serrano M G, Puiu D, Manque P, Akiyoshi D, Mackey A J, Pearson W R, Dear P H, Bankier A T, Peterson D L, Abrahamsen M S, Kapur V, Tzipori S, Buck G A. (2004) The genome of *Cryptosporidium hominis*. Nature 431:1107-12.
5. Abrahamsen M S, Templeton T J, Enomoto S, Abrahante J E, Zhu G, Lancto C A, Deng M, Liu C, Widmer G, Tzipori S, Buck G A, Xu P, Bankier A T, Dear P H, Konfortov B A, Spriggs B F, Iyer L, Anantharaman V, Aravind L, Kapur V. (2004) Complete genome sequence of the apicomplexan, *Cryptosporidium parvum*. Science 304(5669):441-5.

Example 7

Nucleotide Arrays for Detection of *Cryptosporidium* Genes

The array consists of ~4,000 70 base synthetic oligonucleotides bound to glass slides. Each of the ~4,000 *C. hominis* genes is represented by a single, specific oligonucleotide in the array. In order to assess presence or absence of these genes in a biological sample containing putative *Cryptosporidium* parasites, DNA is isolated by standard technology, labeled with fluorescent dyes, and hybridized to the array. A similar DNA sample derived from a known *Cryptosporidium* sample is labeled with an alternative fluorescent dye and used as a control. Both labeled DNAs are hybridized to the same oligonucleotide array, and the arrays are washed and scanned in a fluorescence scanner. The readout of the scanner provides an estimate of the amount of DNA for each gene that is present in the initial sample and a comparison between the two samples. Thus, *Cryptosporidium* genes that are present or absent are determined relative to the control.

The 70 base oligonucleotides in the array were designed by ArrayOligoSelector™ version 3.8.2, (http://arrayoligosel.sourceforge.net/), which selects optimal sequences by:
1. Examining every possible 70 mer sequence from every gene;
2. Using BLASTN (against the whole genome) to check the uniqueness of each 70 mer.
3. Uniqueness is scored as the theoretical binding energy of a candidate oligo to its most similar genome sequence. The binding energy is calculated using a nearest-neighbour model with the established thermodynamic parameters;
4. Using the LZW compression algorithm to calculate the sequence complexity score in bytes between the oligo sequence and the its compressed version;
5. Determining the self-annealing score, calculated as the alignment score of the optimum local alignment between the oligo sequence and its reverse compliment using the Smith-Waterman algorithm;
6. Calculating the GC content of the oligo;
7. Choosing, for each gene, the oligo that maximizes uniqueness and sequence complexity, minimizes self-annealing and has GC content closest to specified by the user; also tries to minimize distance to the 3' end of the gene.

The approximately 4000 oligos and controls designed in this fashion were synthesized commercially and validated in the lab. In the FIG. 3, a hybridization of the array with DNA from *C. hominis* and *C. parvum* was performed to identify *C. hominis* genes that are present or absent in *C. parvum*. Therefore, DNA was purified from *C. hominis* and *C. parvum*, labeled with the fluorescent dyes Cy3 and Cy5, respectively, by indirectly incorporating amino-allyl (aa)-dUTP (Ambion) followed by coupling with fluorescent dyes. Briefly, four micrograms of genomic DNA from each of the two *Cryptosporidium* species was digested with restriction enzyme Hae III, translated with Klenow Exonuclease-free polymerase using random hexamers (pdN6 from Pharmacia) in the presence of aminoallyl-dUTP, and purified to remove the unincorporated nucleotides. The amino-allyl-dUTP labeled DNA samples were dried, dissolved in 0.1 M NaHCO$_3$, pH 9.0, and fluorescently labeled by coupling of the amino allyl-dUTP to Cy3 or Cy5 dyes essentially as described by the manufacturer (Amersham Pharmacia Biotech). The labeled DNAs were hybridized to the oligonucleotide array, which contains approximately 4000 probes representing each of the known *C. hominis* genes. These results demonstrate that the gene complements of *C. hominis* and *C. parvum* show expected similarities, but permit identification of specific genetic differences.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

Lengthy table referenced here

US08114976-20120214-T00001

Please refer to the end of the specification for access instructions.

Lengthy table referenced here

US08114976-20120214-T00002

Please refer to the end of the specification for access instructions.

Lengthy table referenced here

US08114976-20120214-T00003

Please refer to the end of the specification for access instructions.

Lengthy table referenced here

US08114976-20120214-T00004

Please refer to the end of the specification for access instructions.

Lengthy table referenced here

US08114976-20120214-T00005

Please refer to the end of the specification for access instructions.

Lengthy table referenced here

US08114976-20120214-T00006

Please refer to the end of the specification for access instructions.

Lengthy table referenced here

US08114976-20120214-T00007

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US08114976B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08114976B2). An electronic copy of the "Sequence Listing" will also be available from the USPTO upon request and payment of the fee set forth in 37 CFR 1.19(b)(3).

We claim:

1. An isolated nucleic acid molecule encoding the polypeptide set forth as SEQ. ID. NO:8.

2. The isolated nucleic acid molecule of claim 1, wherein said nucleic acid molecule is set forth as SEQ. ID. NO. 7.

* * * * *